United States Patent
Lee et al.

(10) Patent No.: US 10,426,373 B2
(45) Date of Patent: Oct. 1, 2019

(54) MAGNETIC RESONANCE IMAGING APPARATUS AND METHOD OF RECONSTRUCTING MR IMAGE BY USING NEURAL NETWORK

(71) Applicants: SAMSUNG ELECTRONICS CO., LTD., Suwon-si (KR); KOREA ADVANCED INSTITUTE OF SCIENCE AND TECHNOLOGY, Daejeon (KR)

(72) Inventors: Dae-ho Lee, Seongnam-si (KR); Hyun-wook Park, Daejeon (KR); Ki-nam Kwon, Daejeon (KR); Hyun-seok Seo, Seoul (KR)

(73) Assignees: SAMSUNG ELECTRONICS CO., LTD., Suwon-si (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 15/997,074

(22) Filed: Jun. 4, 2018

(65) Prior Publication Data
US 2019/0059780 A1   Feb. 28, 2019

(30) Foreign Application Priority Data

Aug. 25, 2017   (KR) .......................... 10-2017-0108136

(51) Int. Cl.
*A61B 5/055* (2006.01)
*G01R 33/56* (2006.01)
(Continued)

(52) U.S. Cl.
CPC ............ *A61B 5/055* (2013.01); *A61B 5/7207* (2013.01); *A61B 5/7264* (2013.01);
(Continued)

(58) Field of Classification Search
CPC ................ G01R 33/482; G01R 33/546; G01R 33/5608; G01R 33/5611; G01R 33/5615;
(Continued)

(56) References Cited

U.S. PATENT DOCUMENTS 9,841,483 B2 * 12/2017 Wheaton .......... G01R 33/56536
2017/0061620 A1 * 3/2017 Park ....................... G06T 5/001

FOREIGN PATENT DOCUMENTS

JP         2016-97292 A    5/2016
KR   10-2013-0045544 A    5/2013
(Continued)

OTHER PUBLICATIONS

Bruno Di Muzio et al., "Gradient echo sequences", Radiology Reference Article; URL: <http://radiopaedia.org/articles/gradient-echo-sequences-1>, 2005, retrieved on Mar. 21, 2018, 2 pages.
(Continued)

*Primary Examiner* — Manuchehr Rahmjoo
(74) *Attorney, Agent, or Firm* — Sughrue Mion, PLLC

(57) ABSTRACT

A magnetic resonance imaging (MRI) apparatus includes a processor, and a memory storing a program including instructions that, when executed by the processor, cause the processor to acquire first data of a subsampled magnetic resonance (MR) image, acquire, based on a learning model using a neural network, first reconstructed data with respect to rows of pixels in a first phase encoding direction of the first data of the subsampled MR image, and obtain a reconstructed image corresponding to the subsampled MR image, using the first reconstructed data.

20 Claims, 13 Drawing Sheets

(51) Int. Cl.
  *A61B 5/00* (2006.01)
  *G06T 7/00* (2017.01)
  *G01R 33/561* (2006.01)
  *G01R 33/48* (2006.01)
  *G06N 3/08* (2006.01)
  *G01R 33/54* (2006.01)

(52) U.S. Cl.
  CPC ...... *G01R 33/5608* (2013.01); *G01R 33/5611* (2013.01); *G06T 7/0014* (2013.01); *G01R 33/482* (2013.01); *G01R 33/546* (2013.01); *G01R 33/5615* (2013.01); *G06N 3/08* (2013.01); *G06T 2207/10088* (2013.01); *G06T 2207/20081* (2013.01); *G06T 2207/20084* (2013.01)

(58) Field of Classification Search
  CPC ............ G06N 3/08; G06T 2207/10088; G06T 2207/20081; G06T 2207/20084; G06T 7/0014
  See application file for complete search history.

(56) References Cited

FOREIGN PATENT DOCUMENTS

| KR | 10-1659578 B1 | 9/2016 |
|---|---|---|
| KR | 10-2017-0024242 A | 3/2017 |

OTHER PUBLICATIONS

Tim Luijkx et al., "Echo planar imaging", Radiology Reference Article, URL: <http://radiopaedia.org/articles/echo-planar-imaging-1>, 2005, retrieved on Mar. 21, 2018, 2 pages.

Klaas P. Pruessmann et al, "SENSE: Sensitivity Encoding for Fast MRI", Magnetic Resonance in Medicine, vol. 42, Wiley-Liss, Inc., 1999, pp. 952-962.

Mark A. Griswold et al., "Generalized Autocalibrating Partially Parallel Acquisitions (GRAPPA)", Magnetic Resonance in Medicine, vol. 47, Wiley-Liss, Inc., 2002, pp. 1202-1210.

Michael Lustig et al., "Sparse MRI: The Application of Compressed Sensing for Rapid MR Imaging", Magnetic Resonance in Medicine, vol. 58, Wiley-Liss, Inc., 2007, pp. 1182-1195.

Communication dated Sep. 5, 2018 issued by the International Searching Authority in Counterpart Application No. PCT/KR2018/006085 (PCT/ISA/220, PCT/ISA/210, and PCT/ISA/237).

Lee et al., "Deep Residual Learning for Compressed Sensing MRI", 2017, IEEE, 4 pages total, http://arxiv.org/abs/1703.01120.

Communication dated May 31, 2018, issued by the Korean Intellectual Property Office in counterpart Korean Patent Application No. 10-2017-0108136.

Communication dated Aug. 22, 2018, issued by the Korean Intellectual Property Office in counterpart Korean Patent Application No. 10-2017-0108136.

\* cited by examiner

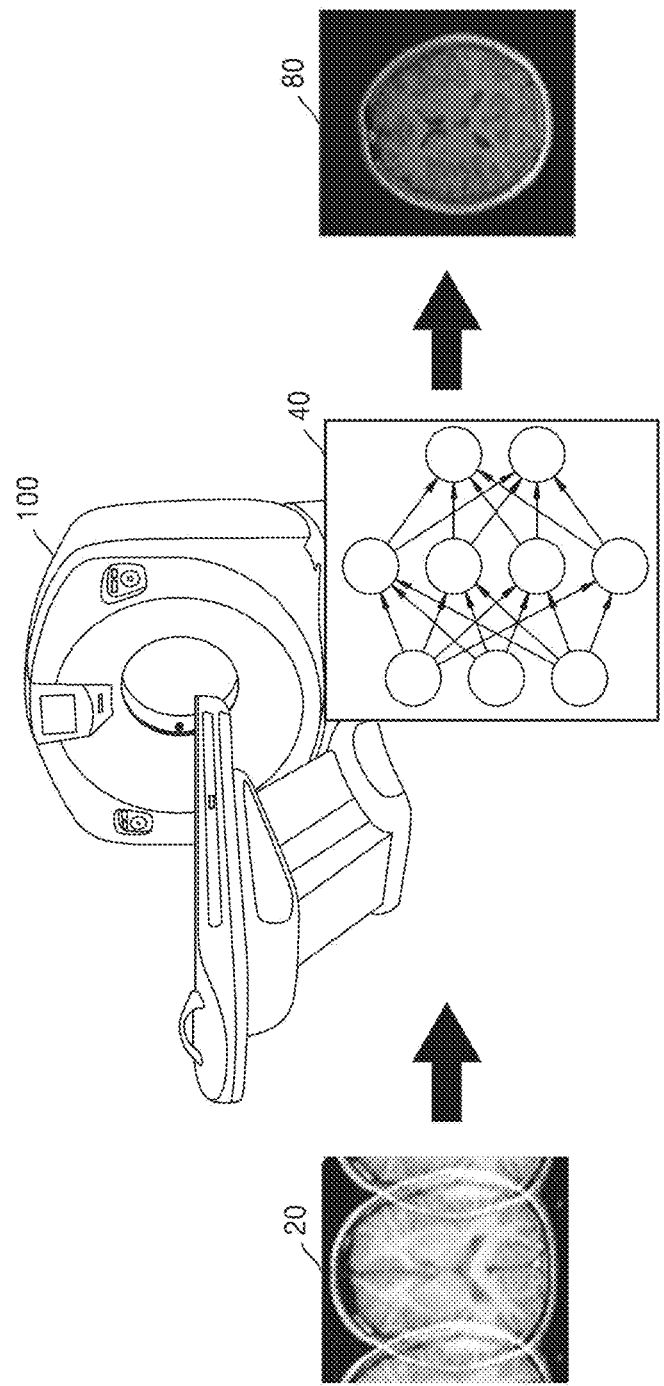

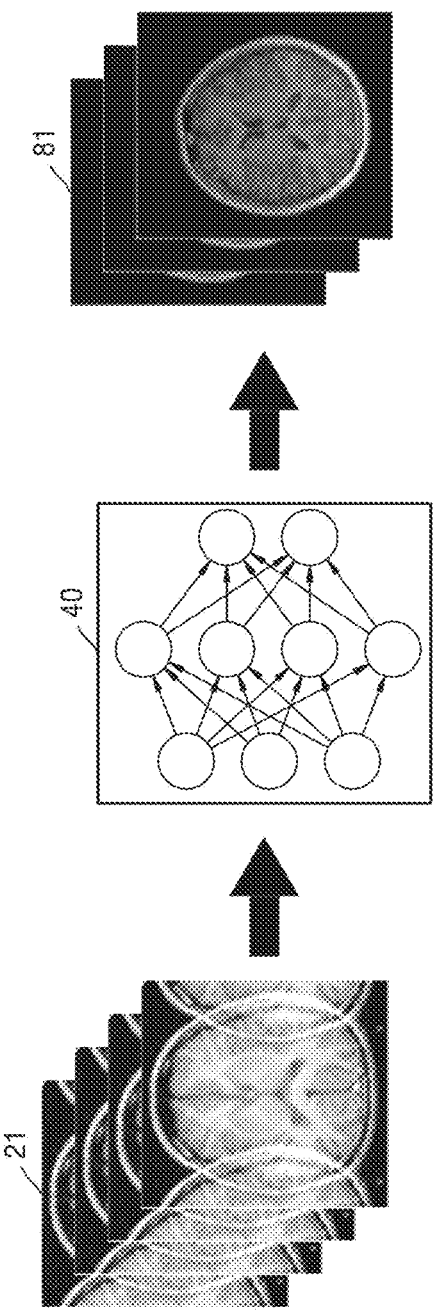

MAGNETIC RESONANCE IMAGING APPARATUS AND METHOD OF RECONSTRUCTING MR IMAGE BY USING NEURAL NETWORK

CROSS-REFERENCE TO RELATED APPLICATION

This application is based on and claims priority under 35 U.S.C. § 119 to Korean Patent Application No. 10-2017-0108136, filed on Aug. 25, 2017, in the Korean Intellectual Property Office, the disclosure of which is incorporated by reference herein in its entirety.

BACKGROUND

1. Field

The disclosure relates to magnetic resonance imaging (MRI) apparatuses and methods of reconstructing MR images, and more particularly, to MRI apparatuses and methods of reconstructing MR images with aliasing artifacts based on a learning model using a neural network.

2. Description of Related Art

An artificial intelligence (AI) system is a computer system exhibiting human-level intelligence, and enables machines to learn and make decisions by themselves and improve their recognition rates through experience.

AI technology consists of a machine learning (deep learning) technique using an algorithm for autonomously classifying/learning features of input data and element techniques for simulating functions of a human brain such as cognition and decision-making by using a machine learning algorithm.

For example, element techniques may include at least one of a linguistic comprehension technique for recognizing human language/characters, a visual comprehension technique for recognizing an object in the same way as performed by a human visual system, a reasoning/prediction technique for judging information and logically reasoning and predicting new information, a knowledge expression technique for processing information about human experience as knowledge data, and an operation control technique for controlling autonomous driving of a vehicle and movement of a robot.

Furthermore, AI techniques have recently been employed for fast reconstruction of medical images (computed tomography (CT) images, magnetic resonance (MR) images, etc.). Various techniques using AI have been used during acquisition of MR images that require a longer acquisition time than other medical images.

SUMMARY

Provided are magnetic resonance imaging (MRI) apparatuses and methods of reconstructing MR images, whereby an MR image acquisition time may be reduced by obtaining a reconstructed MR image corresponding to a subsampled MR image based on a learning model using a neural network.

Additional aspects will be set forth in part in the description that follows and, in part, will be apparent from the description, or may be learned by practice of the presented embodiments.

In accordance with an aspect of the disclosure, an MRI apparatus includes a processor, and a memory storing a program including instructions that, when executed by the processor, cause the processor to acquire first data of a subsampled magnetic resonance (MR) image, acquire, based on a learning model using a neural network, first reconstructed data with respect to rows of pixels in a first phase encoding direction of the first data of the subsampled MR image, and obtain a reconstructed image corresponding to the subsampled MR image, using the first reconstructed data.

In accordance with another aspect of the disclosure, an image reconstruction method includes acquiring first data of a subsampled magnetic resonance (MR) image, acquiring, based on a learning model using a neural network, first reconstructed data with respect to rows of pixels in a first phase encoding direction of the first data of the subsampled MR image, and obtaining a reconstructed image corresponding to the subsampled MR image, using the first reconstructed data.

In accordance with another aspect of the disclosure, a computer program product includes a non-transitory computer-readable recording medium recording a program for executing the image reconstruction method on a computer.

In accordance with another aspect of the disclosure, an MRI apparatus includes a processor, and a memory storing a program including instructions that, when executed by the processor, cause the processor to acquire first data of a subsampled magnetic resonance (MR) image, acquire, based on a learning model using a neural network, reconstructed data with respect to rows of pixels in a direction in which aliasing occurs in the first data of the subsampled MR image, and obtain a reconstructed image corresponding to the subsampled MR image, using the reconstructed data.

In accordance with another aspect of the disclosure, an image reconstruction method includes acquiring first data of a subsampled magnetic resonance (MR) image, acquiring, based on a learning model using a neural network, reconstructed data with respect to rows of pixels in a direction in which aliasing occurs in the first data of the subsampled MR image, and obtaining a reconstructed image corresponding to the subsampled MR image, using the reconstructed data.

BRIEF DESCRIPTION OF THE DRAWINGS

The above and other aspects, features, and advantages of embodiments of the disclosure will be more apparent from the following description, taken in conjunction with the accompanying drawings, in which:

FIG. 1A is a schematic diagram for explaining an image reconstruction method according to an embodiment;

FIG. 1B is a diagram for explaining a process of building a learning model by using a neural network, according to an embodiment;

DETAILED DESCRIPTION

Figure 2:
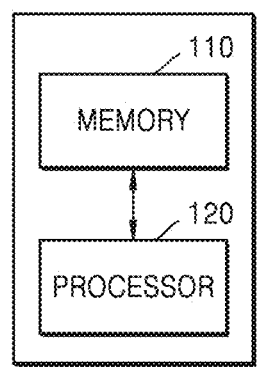
FIG. 2 is a block diagram of a configuration of a magnetic resonance imaging (MRI) apparatus according to an embodiment.

The present specification describes principles of the disclosure and sets forth embodiments thereof to clarify the scope of the disclosure and to allow those of ordinary skill in the art to implement the embodiments. The present embodiments may have different forms.

Like reference numerals refer to like elements throughout. The present specification does not describe all components in the embodiments, and common knowledge in the art or the same descriptions of the embodiments will be omitted below. The term "part" or "portion" may be implemented using hardware or software, and according to embodiments, one "part" or "portion" may be formed as a single unit or element or include a plurality of units or elements. Hereinafter, the principles and embodiments of the disclosure will be described in detail with reference to the accompanying drawings. Expressions such as "at least one of," when preceding a list of elements, use the entire list of elements and do not use the individual elements of the list.

In the present specification, an "image" may include a medical image obtained by a magnetic resonance imaging (MRI) apparatus, a computed tomography (CT) apparatus, an ultrasound imaging apparatus, an X-ray apparatus, or another medical imaging apparatus.

Furthermore, in the present specification, an "object" may be a target to be imaged and include a human, an animal, or a part of a human or animal. For example, the object may include a body part (an organ) or a phantom.

An MRI system acquires an MR signal and reconstructs the acquired MR signal into an image. The MR signal denotes a radio frequency (RF) signal emitted from the object.

In the MRI system, a main magnet creates a static magnetic field to align a magnetic dipole moment of a specific atomic nucleus of the object placed in the static magnetic field along a direction of the static magnetic field. A gradient coil may generate a gradient magnetic field by applying a gradient signal to a static magnetic field and induce resonance frequencies differently according to each region of the object.

An RF coil may emit an RF signal to match a resonance frequency of a region of the object whose image is to be acquired. Furthermore, when gradient magnetic fields are applied, the RF coil may receive MR signals having different resonance frequencies emitted from a plurality of regions of the object. Though this process, the MRI system may obtain an image from an MR signal by using an image reconstruction technique.

FIG. 1A is a schematic diagram for explaining an image reconstruction method according to an embodiment.

Referring to FIG. 1A, an MRI apparatus 100 according to an embodiment may obtain a reconstructed image 80 corresponding to a subsampled MR image 20 based on a learning model created using a neural network 40.

In this case, the subsampled MR image 20 may be an image corresponding to input data that is provided to the MRI apparatus 100 to obtain the reconstructed image 80. Furthermore, the subsampled MR image 20 is acquired by sampling MR signals at a sampling rate lower than the Nyquist sampling rate. The subsampled MR image 20 may be an image with aliasing artifacts.

According to an embodiment, the MRI apparatus 100 may acquire input data corresponding to the subsampled MR image 20 based on MR signals received from RF coils.

According to another embodiment, the MRI apparatus 100 may acquire input data corresponding to the subsampled MR image 20 from at least one of an external MRI apparatus, an external server, and a database.

In this case, the input data may include an MR signal received from an RF coil. Furthermore, the input data may include subsampled k-space data generated by arranging subsampled MR signals in a k-space. Furthermore, the input data may include image data generated by performing Fourier transform on the subsampled k-space data.

The reconstructed image 80 may be an image corresponding to output data acquired when the subsampled MR image 20 corresponding to the input data is input to the MRI apparatus 100. The reconstructed image 80 may be obtained by removing aliasing artifacts from the subsampled MR image 20.

In an embodiment, examples of the MRI apparatus 100 may include, but are not limited to, an MRI apparatus capable of autonomously obtaining an MR image, an image processing apparatus for processing an image acquired from the outside, a smartphone, a tablet personal computer (PC), a PC, a smart television (TV), a mobile phone, a personal digital assistant (PDA), a laptop, a micro server, an electronic book terminal, a home appliance, and other mobile or non-mobile computing devices having a processing function for an MR image. Furthermore, the MRI apparatus 100 may be a wearable device such as a watch, glasses, a hair band, or a ring having a communication function and a data processing function.

FIG. 1B is a diagram for explaining a process of building a learning model by using the neural network 40, according to an embodiment.

Referring to FIG. 1B, the neural network 40 may be a set of algorithms that learn a correlation between at least one subsampled MR image 21 and at least one fully sampled MR image 81 by using statistical machine learning results. The neural network 40 may include at least one neural network.

The neural network 40 may include network models such as deep neural network (DNN), recurrent neural network (RNN), bidirectional recurrent deep neural network (BRDNN), multilayer perceptron (MLP), and convolutional neural network (CNN), but is not limited thereto.

Furthermore, a learning model may be a model created by learning correlations between the at least one subsampled MR image 21 and the at least one fully sampled MR image 81 based on the neural network 40.

For example, the learning model may be a model that is created by learning correlations between the at least one subsampled MR image 21 and the at least one fully sampled MR image 81 based on the neural network 40 in units of at least one row of pixels corresponding to a phase encoding direction.

The at least one fully sampled MR image 81 may be separately obtained for creating the learning model. Furthermore, the at least one fully sampled MR image 81 may be obtained by sampling k-space data at a rate higher than or equal to the Nyquist sampling rate.

The at least one subsampled MR image 21 may be acquired by sampling k-space data at a rate lower than the Nyquist sampling rate.

According to an embodiment, each of the at least one subsampled MR image 21 may be acquired by sampling k-space data corresponding to the corresponding fully sampled MR image 81 at a rate lower than the Nyquist sampling rate. Furthermore, the at least one subsampled MR image 21 may be acquired simultaneously with the at least one fully sampled MR image 81.

According to an embodiment, the learning model may be created using various additional data other than the at least one subsampled MR image 21 and the at least one fully sampled MR image 81. For example, at least one of sensitivity information of a multi-channel RF coil and k-space data, real image data, magnitude image data and phase image data corresponding to the at least one subsampled MR image 21 may be used as additional data.

According to an embodiment, the MRI apparatus 100 may autonomously create the above-described learning model.

According to another embodiment, the MRI apparatus 100 may acquire a learning model created in an external server or device from the external server or device.

According to embodiments, the MRI apparatus 100 may obtain a reconstructed image 80 corresponding to the subsampled MR image 20 based on a learning model using the neural network 40 described with reference to FIG. 1B, thereby preventing a degradation of an image quality due to acceleration of image acquisition.

FIG. 2 is a block diagram of a configuration of an MRI apparatus 100 according to an embodiment.

The MRI apparatus 100 of FIG. 2 may be an apparatus capable of accelerating acquisition of an MR image by obtaining the reconstructed image (80 of FIG. 1A) corresponding to the subsampled MR image (20 of FIG. 1A) by using at least one neural network (40 of FIG. 1A).

Referring to FIG. 2, the MRI apparatus 100 includes a memory 110 and a processor 120. The processor 120 may correspond to a processor 1100 that will be described below with reference to FIG. 11. Furthermore, the processor 120 may correspond to one or a combination of an image processing unit 11 and a controller 30 that will be described below with reference to FIG. 14.

The memory 110 may store various pieces of data, programs, or applications for driving and controlling the MRI apparatus 100. The programs stored in the memory 110 may include one or more instructions. The programs (the one or more instructions) or applications stored in the memory 110 may be executed by the processor 120.

According to an embodiment, the memory 110 may include one or more instructions that make up the neural network 40. Furthermore, the memory 110 may include one or more instructions for controlling the neural network 40. The neural network 40 may be composed of a plurality of layers including one or more instructions and that learn correlations between the at least one subsampled MR image (41 of FIG. 1B) and the at least one fully sampled MR image (81 of FIG. 1B) in units of at least one row of pixels corresponding to a phase encoding direction. Furthermore, the neural network 40 may include a plurality of input channels for performing parallel learning with respect to a plurality of inputs.

The processor 120 may execute at least one program stored in the memory 110. When a previously set and stored condition is satisfied, the processor 120 may execute an operating system (OS) and various programs stored in the memory 110. The processor 120 may include at least one processor including a single core, dual cores, triple cores, quad cores, or a multiple number of cores. Furthermore, for example, the processor 120 may be implemented by a main processor and a sub processor that operates in a sleep mode.

The processor 120 may acquire data of the subsampled MR image 20. The subsampled MR image 20 may be an image corresponding to input data used for the processor 120 to obtain the reconstructed image 80.

The data of the subsampled MR image 20 may include an MR signal received from an RF coil. Furthermore, the data of the subsampled MR image 20 may include subsampled k-space data generated by arranging subsampled MR signals in a k-space. In addition, the data of the subsampled MR image 20 may include image data generated by performing Fourier transform on subsampled k-space data.

For example, the processor 120 may acquire MR signals subsampled in a regular or irregular pattern via RF coils included in the MRI apparatus 100 and then data of the subsampled MR image 20 based on the acquired MR signals. As another example, the processor 120 may acquire data of the subsampled MR image 20 from at least one of an external server, a database, and an external MRI apparatus.

The processor 120 acquires, based on a learning model using the at least one neural network 40, reconstructed data with respect to at least one row of pixels corresponding to a phase encoding direction of data of the subsampled MR image 20.

The processor 120 may acquire, based on a learning model using the at least one neural network 40, reconstructed data by reconstructing data corresponding to the subsampled MR image 20 in units of at least one row of pixels corresponding to a phase encoding direction.

According to an embodiment, the processor 120 may divide data of the subsampled MR image 20 into a plurality of groups, each group including at least one row of pixels corresponding to a phase encoding direction. A phase encoding direction of the subsampled MR image 20 may be parallel to a direction in which aliasing artifacts occur in the subsampled MR image 20.

Furthermore, dividing the data of the subsampled MR image 20 into groups, each with at least one row of pixels corresponding to a phase encoding direction, may mean dividing the data of the subsampled MR image 20 into groups, each with at least one row of pixels parallel to the phase encoding direction.

For example, when the phase encoding direction is parallel to an x-axis direction of an image plane, the processor 120 may divide the data of the subsampled MR image 20 into a plurality of groups, each with one row of pixels having the same value on a y-axis. Furthermore, the processor 120 may split the data of the subsampled MR image 20 into a plurality of groups, each including a plurality of rows of pixels respectively having the same values on the y-axis.

Similarly, when the phase encoding direction is parallel to a y-axis direction of an image plane, the processor 120 may divide the data of the subsampled MR image 20 into a plurality of groups, each with one row of pixels having the same value on an x-axis.

According to an embodiment, a grouping method, according to which the processor 120 determines whether each group is composed of one row or a plurality of rows of pixels corresponding to a phase encoding direction of the data of the subsampled MR image 20, may be determined dynamically by the neural network 40. Dynamically determining the grouping method by using the neural network 40 may mean determining the most effective grouping method based on a statistical error of the reconstructed image 80 obtained according to the grouping method for the data of the subsampled MR image 20.

The processor 120 may acquire pieces of reconstructed data respectively corresponding to the plurality of groups for the data of the subsampled MR image 20 based on a learning model using the neural network 40.

The reconstructed data may be acquired by applying a learning model to the plurality of groups for the data of the subsampled MR image 20. The reconstructed data may include parameters or weight values used to acquire data of the reconstructed image 80 based on the data of the subsampled MR image 20, but is not limited thereto. Furthermore, applying the learning model to the plurality of groups may mean providing data with respect to the plurality of groups to the MRI apparatus 100 as input data for obtaining the reconstructed image 80.

For example, the processor 120 may sequentially acquire pieces of reconstructed data respectively corresponding to the plurality of groups based on the learning model using the neural network 40. As another example, the processor 120 may acquire pieces of reconstructed data respectively corresponding to groups in the plurality of groups in parallel by using the neural network 40 including a plurality of input channels. The processor 120 may acquire reconstructed data corresponding to the entire subsampled MR image 20 based on the pieces of reconstructed data respectively corresponding to the plurality of groups.

It has been described in the above-described embodiments that the processor 120 acquires reconstructed data with respect to at least one row of pixels corresponding to a phase encoding direction of data of the subsampled MR image 20, or divides the data of the subsampled MR image 20 into a plurality of groups, each with at least one row of pixels corresponding to the phase encoding direction, to acquire pieces of reconstructed data respectively corresponding to the plurality of groups based on a learning model using the neural network 40. However, embodiments of the disclosure are not limited thereto. The processor 120 may acquire reconstructed data by reconstructing the data of the subsampled MR image 20 in units of at least one pixel, based on a learning model using the neural network 40.

The processor 120 obtains the reconstructed image 80 corresponding to the subsampled MR image 20 based on the acquired reconstructed data. The processor 120 may obtain the reconstructed image 80 as output data for the subsampled MR image 20 corresponding to input data. The reconstructed image 80 may mean an image obtained by removing aliasing artifacts occurring in the phase encoding direction from the subsampled MR image 20.

According to an embodiment, the MRI apparatus 100 may further include a multi-channel RF coil. Coil elements in the multi-channel RF coil may respectively receive MR signals from an object.

According to an embodiment, the processor 120 may acquire subsampled MR images based on MR signals respectively received via the coil elements in the multi-coil RF coil.

According to an embodiment, the learning model using the neural network 40 may be created by learning correlations between subsampled MR images corresponding to the MR signals respectively acquired via the coil elements in the multi-channel RF coil and at least one fully sampled MR image in units of at least one row of pixels corresponding to a phase encoding direction.

Furthermore, the learning model may be created by additionally using sensitivity information of a multi-channel RF coil during a learning process. Accordingly, the processor 120 may obtain the reconstructed image 80 based on the learning model using the neural network 40 by using sensitivity information of the multi-channel RF coil, other than the subsampled MR image 20, as additional input data.

According to embodiments, even when acquiring only input data corresponding to the subsampled MR image 20, the MRI apparatus 100 may obtain the reconstructed image 80 corresponding to the subsampled MR image 20 based on a learning model using the neural network 40. Accordingly, the MRI apparatus 100 may accelerate acquisition of an MR image to be used for diagnosis.

Figure 3:
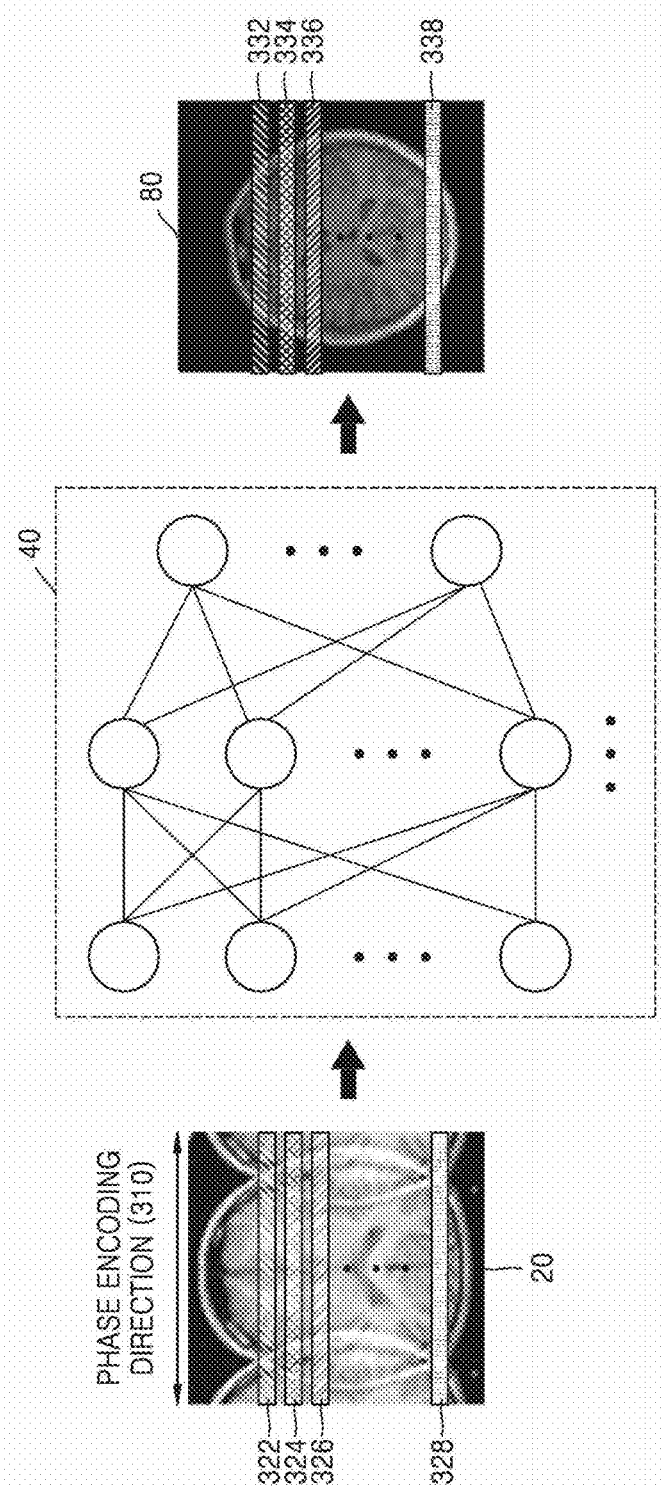
FIG. 3 illustrates a process of acquiring reconstructed data corresponding to a subsampled MR image based on a learning model using a neural network, according to an embodiment.

FIG. 3 illustrates a process of acquiring reconstructed data corresponding to a subsampled MR image 20 based on a learning model using the neural network 40, according to an embodiment.

The MRI apparatus (100 of FIG. 2) acquires the subsampled MR image 20. The MRI apparatus 100 acquires, based on the learning model using the at least one neural network 40, reconstructed data with respect to at least one row of pixels corresponding to a phase encoding direction 310 of data of the subsampled MR image 20.

The MRI apparatus 100 may acquire, based on the learning model using the at least one neural network 40, reconstructed data by reconstructing the data of the subsampled MR image 20 in units of at least one row of pixels corresponding to the phase encoding direction 310.

According to an embodiment, the MRI apparatus 100 may divide the data of the subsampled MR image 20 corresponding to input data into a plurality of groups, each with one row of pixels corresponding to the phase encoding direction 310.

As described above, a method, performed by the MRI apparatus 100, of dividing the data of the subsampled MR image 20 into a plurality of groups may be determined dynamically by the at least one neural network 40.

An example in which the MRI apparatus 100 divides the data of the subsampled MR image 20 into a plurality of groups, each with one row of pixels corresponding to the phase encoding direction 310, will now be described.

For example, when the subsampled MR image 20 has a size of 256*256, the MRI apparatus 100 may divide the data of the subsampled MR image 20 into 256 groups 322, 324, 326, . . . , and 328 parallel to the phase encoding direction 310. Furthermore, the MRI apparatus 100 may acquire, based on the learning model using the at least one neural network 40, pieces of reconstructed data 332, 334, 336, . . . , and 338 respectively corresponding to the plurality of groups 322, 324, 326, . . . , and 328.

According to an embodiment, the MRI apparatus 100 may respectively acquire the pieces of reconstructed data 332, 334, 336, . . . , and 338 by applying a method corresponding to a learning method used to create the learning model using the at least one neural network 40 to groups included in the plurality of groups 322, 324, 326, . . . , and 328 in a sequential or parallel manner.

The MRI apparatus 100 may obtain the reconstructed image 80 corresponding to the subsampled MR image 20 based on the pieces of reconstructed data 332, 334, 336, . . . , and 338 respectively corresponding to the plurality of groups 322, 324, 326, . . . , and 328.

Figure 4:
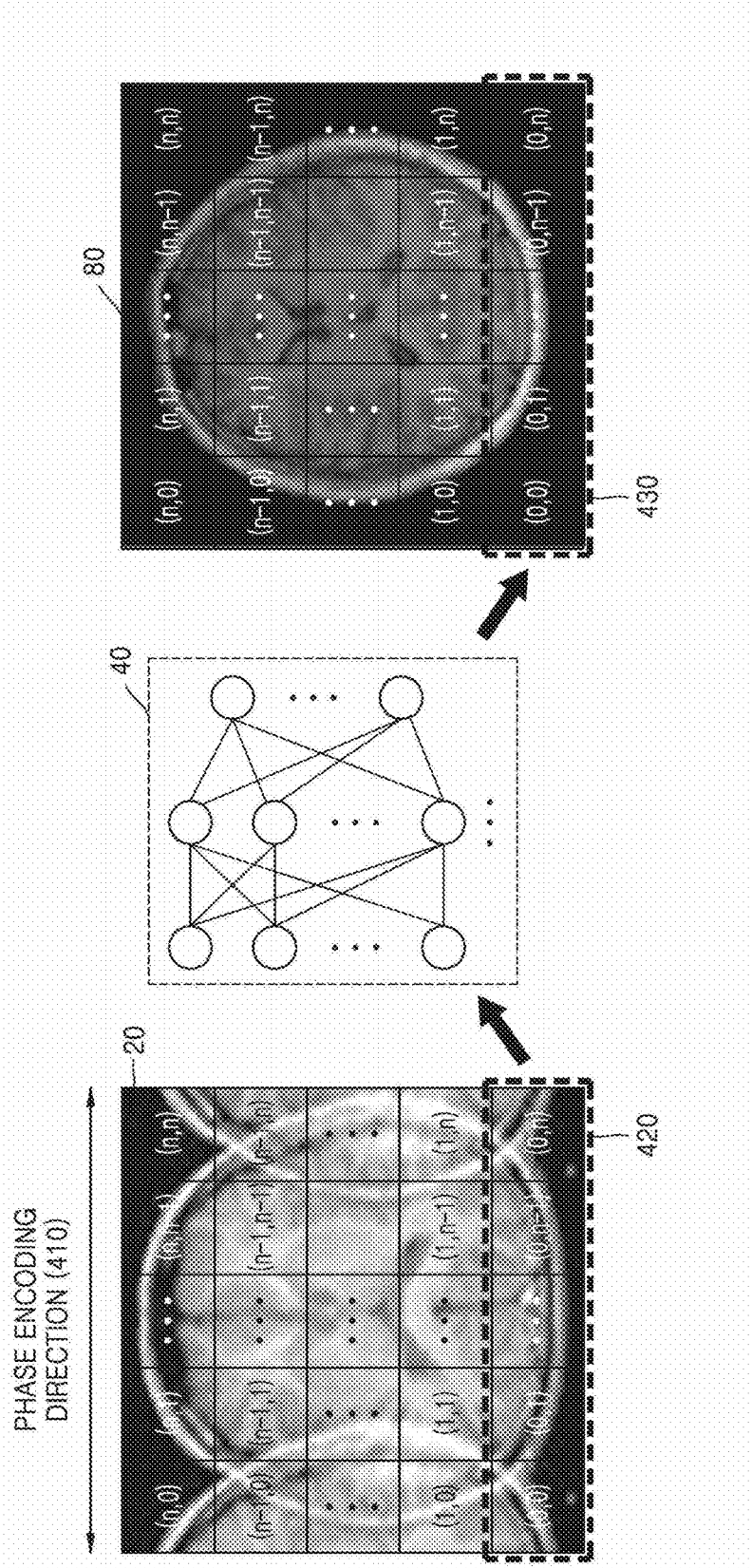
FIG. 4 is a diagram for explaining a method of dividing data of a subsampled MR image into groups, according to an embodiment.

FIG. 4 is a diagram for explaining a method of dividing data of the subsampled MR image 20 into groups, according to an embodiment.

Referring to FIG. 4, the MRI apparatus 100 may divide data of the subsampled MR image 20 into a plurality of groups, each with at least one row of pixels corresponding to a phase encoding direction 410.

The subsampled MR image 20 may include (n+1)*(n+1) pixels (n is a natural number). For example, n+1=256. Furthermore, the phase encoding direction 410 may be parallel to a direction in which aliasing artifacts occur in the subsampled MR image 20. The MRI apparatus 100 determine a single row of pixels {(0,0), (0, 1), (0, 2), . . . , and (0, n)} 420 corresponding to the phase encoding direction 410 among the (n+1)*(n+1) pixels as one group and, in the same manner, determine n groups, each including {(1,0), (1, 1), (1, 2), . . . , and (1, n)}, . . . , or {(n,0), (n, 1), (n, 2), . . . , and (n, n)}.

The MRI apparatus 100 may acquire reconstructed data {(0,0), (0, 1), (0, 2), . . . , and (0, n)} 430 corresponding to the row of pixels {(0,0), (0, 1), (0, 2), . . . , and (0, n)} 420 that form one of the n+1 groups in the subsampled MR image 20.

According to an embodiment, the reconstructed data {(0,0), (0, 1), (0, 2), . . . , and (0, n)} 430 corresponding to {(0,0), (0, 1), (0, 2), . . . , and (0, n)} 420 that is one of the n+1 groups in the data of the subsampled MR image 20 may be pixel values at positions corresponding to {(0,0), (0, 1), (0, 2), . . . , and (0, n)} in the reconstructed image 80 corresponding to the subsampled MR image 20.

According to another embodiment, the reconstructed data {(0,0), (0, 1), (0, 2), . . . , and (0, n)} 430 corresponding to {(0,0), (0, 1), (0, 2), . . . , and (0, n)} 420 that is one of the n+1 groups in the data of the subsampled MR image 20 may be parameters or weight values that can be used to obtain pixel values at positions corresponding to {(0,0), (0, 1), (0, 2), . . . , and (0, n)} in the reconstructed image 80 corresponding to the subsampled MR image 20.

Based on the above-described methods, the MRI apparatus 100 may acquire pieces of reconstructed data respectively corresponding to the n+1 groups in the data of the subsampled MR image 20. The MRI apparatus 100 may then obtain the reconstructed image 80 corresponding to the subsampled MR image 20 based on the pieces of reconstructed data respectively corresponding to the n+1 groups.

Although FIG. 4 illustrates a grouping method according to which the data of the subsampled MR image 20 is divided into the n+1 groups, each including one row of pixels corresponding to the phase encoding direction 410, embodiments are not limited thereto. For example, the MRI apparatus 100 may divide data of the subsampled MR image 20 into half of the n+1 groups, each group having two rows of pixels corresponding to the phase encoding direction 410. The grouping method may be dynamically determined by the at least one neural network 40 as an optimal method for obtaining the reconstructed image 80 based on statistical machine learning results.

According to embodiments, the MRI apparatus 100 may acquire, based on the learning model using the at least one neural network 40, reconstructed data corresponding to the subsampled MR image 20 in units of at least one row of pixels corresponding to the phase encoding direction 410 of the subsampled MR image 20, thereby obtaining the reconstructed image 80 through a relatively small number of mathematical operations. The subsampled MR image 20 may contain aliasing artifacts in a direction parallel to the phase encoding direction 410 in which subsampling occurs due to an insufficient number of data in the phase encoding direction 410. On the other hand, because all data are acquired in a frequency encoding direction along which data readout occurs in a k-space, data loss may not occur in a direction corresponding to the frequency encoding direction, and accordingly, aliasing artifacts may not be introduced in that direction.

Thus, when the MRI apparatus 100 performs a mathematical operation for acquiring reconstructed data by constructing input data in a direction corresponding to a phase encoding direction in which aliasing artifacts occur before obtaining the reconstructed image 80 corresponding to the subsampled MR image 20, it is possible to acquire reconstructed data without performing unnecessary mathematical operations related to the frequency encoding direction in which all the data have already been acquired.

Accordingly, according to embodiments, the MRI apparatus 100 may intensively perform mathematical operations related to the phase encoding direction requiring reconstruction of data, based on the learning model using the at least one neural network 40, thereby increasing acquisition efficiency and quality of the reconstructed image 80.

Figure 5:
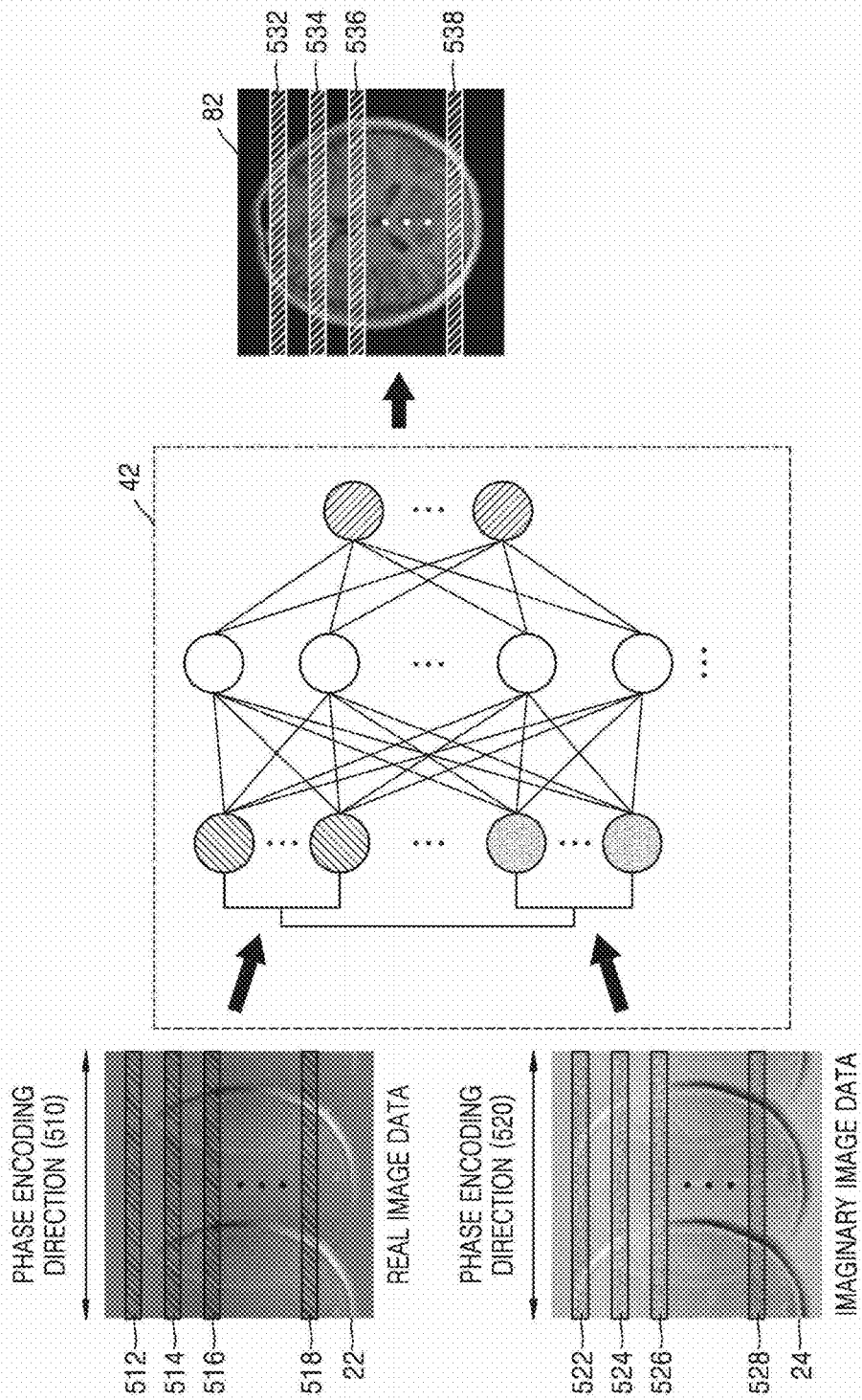
FIG. 5 illustrates a process of acquiring reconstructed data corresponding to a subsampled MR image based on a learning model using a neural network, according to another embodiment.

FIG. 5 illustrates a process of acquiring reconstructed data corresponding to a subsampled MR image based on a learning model using a neural network 42, according to another embodiment.

Referring to FIG. 5, the MRI apparatus 100 may acquire real image data 22 and imaginary image data 24 corresponding to the subsampled MR image. The MRI apparatus 100 may acquire the real image data 22 and the imaginary image data 24 as input data for obtaining a reconstructed image 82 corresponding to the subsampled MR image.

The real image data 22 may be data regarding a real part of k-space data corresponding to the subsampled MR image. The imaginary image data 24 may be data regarding an imaginary part of the k-space data corresponding to the subsampled MR image.

The neural network 42 may be implemented as a neural network including multiple input channels as shown in FIG. 5.

The MRI apparatus 100 may respectively acquire pieces of reconstructed data with respect to at least one row of pixels corresponding to a phase encoding direction 510 of the real image data 22 and their corresponding pixels in the imaginary image data 24. The MRI apparatus 100 may determine data with respect to the at least one row of pixels corresponding to the phase encoding direction 510 of the real image data 22 and data with respect to their corresponding pixels in the imaginary image data 24 as being input data for different input channels of the neural network 42.

According to an embodiment, the MRI apparatus 100 may divide the real image data 22 into a plurality of groups 512, 514, . . . , and 518, each including at least one row of pixels corresponding to the phase encoding direction 510. Furthermore, the MRI apparatus 100 may divide the imaginary image data 24 into a plurality of groups 522, 524, . . . , and 528, each including at least one row of pixels corresponding to a phase encoding direction 520. The grouping method for the real image data 22 and the imaginary image data 24 may correspond to the grouping method for the data of the subsampled MR image described with reference to FIGS. 3 and 4, and thus descriptions already provided above with respect to FIGS. 3 and 4 will be omitted here.

The phase encoding directions 510 and 520 of the real image data 22 and the imaginary image data 24 may respectively correspond to phase encoding directions of the subsampled MR image. Furthermore, the phase encoding directions 510 and 520 of the real image data 22 and the imaginary image data 24 may respectively correspond to directions in which aliasing artifacts occur in the subsampled MR image.

In an embodiment, the MRI apparatus 100 may respectively determine one of the plurality of groups 512, 514, . . . , and 518 in the real image data 22 and its corresponding group in the imaginary image data 24 as input data for different input channels of the neural network 42. Furthermore, the MRI apparatus 100 may acquire, based on the learning model using the neural network 42, reconstructed data with respect to the one group in the real image data 22 and its corresponding group in the imaginary image data 24.

For example, a group 512 included in the plurality of groups 512, 514, . . . , and 518 may correspond to a group 522 among the plurality of groups 522, 524, . . . , and 528 in the imaginary image data 24. The MRI apparatus 100 may determine the groups 512 and 522 as input data for different input channels of the neural network 42. Furthermore, the MRI apparatus 100 may acquire reconstructed data 532 with respect to the groups 512 and 522 based on the learning model using the neural network 42. According to the above-described method, when each of the plurality of groups 512, 514, . . . , and 518 in the real image data 22 and its corresponding group in the imaginary image data 24 are provided as an input for different channels, the MRI apparatus 100 may acquire pieces of reconstructed data 532, 534, 536, . . . , and 538 based on the learning model using the neural network 42. The MRI apparatus 100 may then obtain the reconstructed image 82 corresponding to the subsampled MR image based on the acquired pieces of reconstructed data 532, 534, 536, . . . , and 538.

According to embodiments, by using the real image data 22 and the imaginary image data 24 of the subsampled MR image as input data for the learning model using the neural network 42, the MRI apparatus 100 may obtain the reconstructed image 82 corresponding to the subsampled MR image without data loss due to phase overlapping.

According to another embodiment, the MRI apparatus 100 may acquire magnitude image data and phase image data corresponding to the subsampled MR image. The MRI apparatus 100 may acquire magnitude image data and phase image data as input data for obtaining the reconstructed image 82 corresponding to the subsampled MR image.

The MRI apparatus 100 may acquire pieces of reconstructed data with respect to at least one row of pixels corresponding to a phase encoding direction of magnitude image data and their corresponding pixels in phase image data. The MRI apparatus 100 may determine data with respect to the at least one row of pixels corresponding to the phase encoding direction of the magnitude image data and data with respect to their corresponding pixels in the phase image data as being input data for different input channels of the neural network 42.

Furthermore, the MRI apparatus 100 may respectively divide the acquired magnitude image data and phase image data into a plurality of groups, each including at least one row of pixels corresponding to a phase encoding direction, according to the above-described grouping method.

According to an embodiment, similarly to corresponding groups in the real image data 22 and the imaginary image data 24, the MRI apparatus 100 may determine groups in the magnitude image data and the phase image data as input data for different channels of the neural network 42.

According to another embodiment, the MRI apparatus 100 may determine only one group in magnitude image data and its corresponding group in phase image data as input data for different channels. The MRI apparatus 100 may determine groups in the magnitude image data and the phase image data as input data for the learning model using the neural network 42 to thereby acquire reconstructed data and the reconstructed image 82 corresponding to the subsampled MR image.

Figure 6:
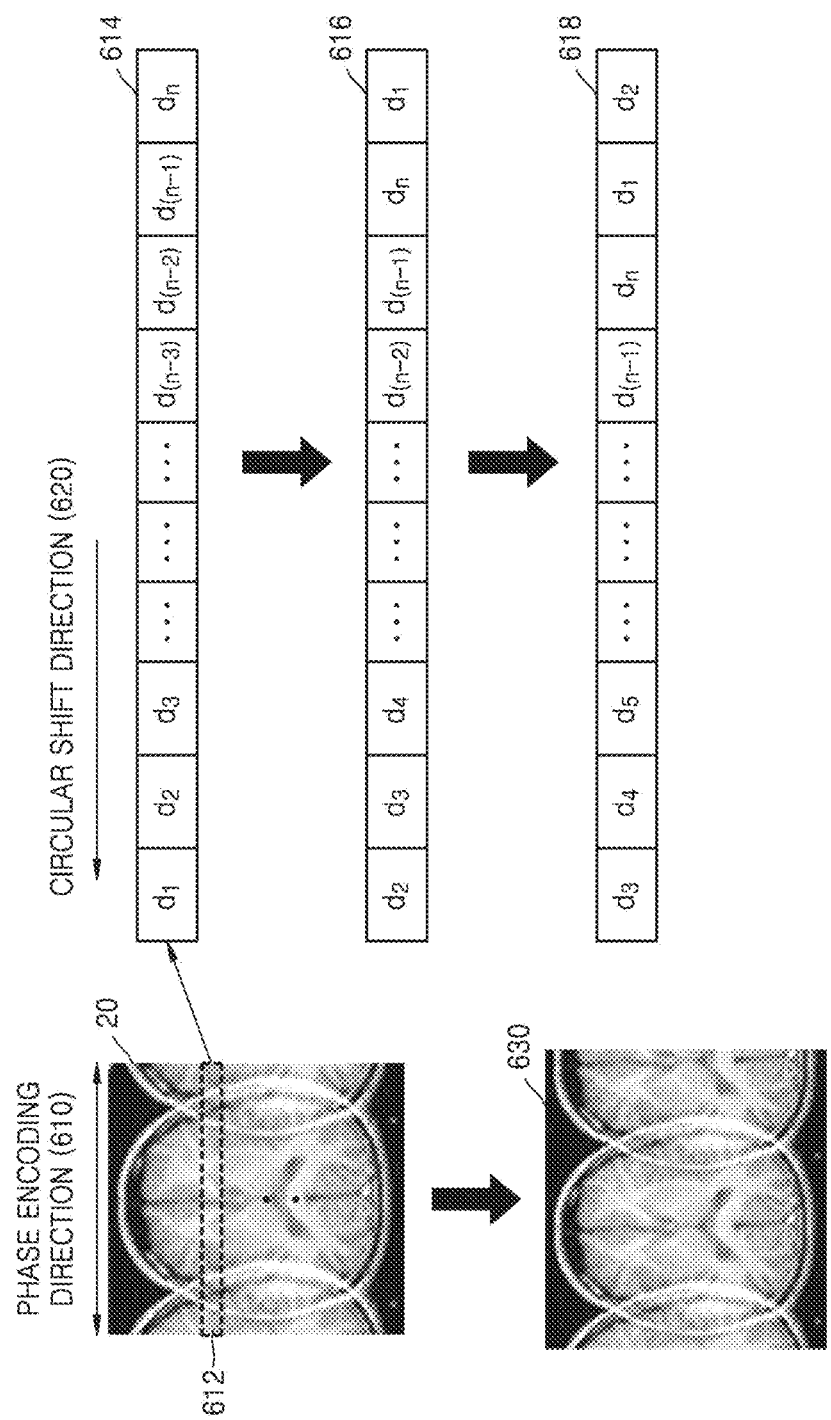
FIG. 6 is diagram for explaining a method, performed by an MRI apparatus, of acquiring data of at least one additional image by using circular shifting, according to an embodiment.

FIG. 6 is diagram for explaining a method, performed by the MRI apparatus 100, of acquiring data of at least one additional image by using circular shifting, according to an embodiment.

FIG. 6 illustrates a method, performed by the MRI apparatus 100, of circularly shifting data of the subsampled MR image 20 by one or two pixels to acquire data of at least one additional image. Circular shifting of data is a kind of data carryover, which may mean that data such as a number, a letter, a word, etc. shifted out of one end is inserted into the opposite end.

According to an embodiment, the MRI apparatus 100 may circularly shift the data of the subsampled MR image 20 in a direction parallel to a phase encoding direction 610. The MRI apparatus 100 may acquire data of an additional image 630 obtained by circularly shifting the data of the subsampled MR image 20 by at least one pixel in one of the left and right directions parallel to the phase encoding direction 610.

For example, the MRI apparatus 100 may circularly shift the data of the subsampled MR image 20 by one pixel in the right direction that is a circular shift direction 620. In this case, arrangement of data in a group 612 in the subsampled MR image 20 may be changed from {d1, d2, d3, . . . , d(n−3), d(n−2), d(n−1), dn} 614 to {d2, d3, . . . , d(n−3), d(n−2), d(n−1), dn, d1} 616, Furthermore, when the MRI apparatus 100 circularly shifts the data of the subsampled MR image 20 by two pixels in the circular shift direction 620, arrangement of the data in the group 612 in the subsampled MR image 20 may be changed from {d1, d2, d3, . . . , d(n−3), d(n−2), d(n−1), dn} 614 to {d3, . . . , d(n−3), d(n−2), d(n−1), dn, d1, d2} 618.

Furthermore, although now shown in FIG. 6, according to another embodiment, the MRI apparatus 100 may acquire data of at least one additional image by rotating the data of the subsampled MR image 20 around a center of the subsampled MR image 20 by at least one degree.

As described above, the MRI apparatus 100 may acquire data of at least one additional image corresponding to the subsampled MR image 20 by circularly shifting data or rotating data around the center of the subsampled MR image 20. The MRI apparatus 100 may use data of the at least one additional image corresponding to the subsampled MR image 20 as input data for obtaining the reconstructed image (80 of FIG. 3). By acquiring data of the at least one additional image and using the data of the at least one additional image as input data for the learning model, the MRI apparatus 100 may obtain the reconstructed image 80 with relatively high accuracy from even a small amount of input data.

Figure 7:
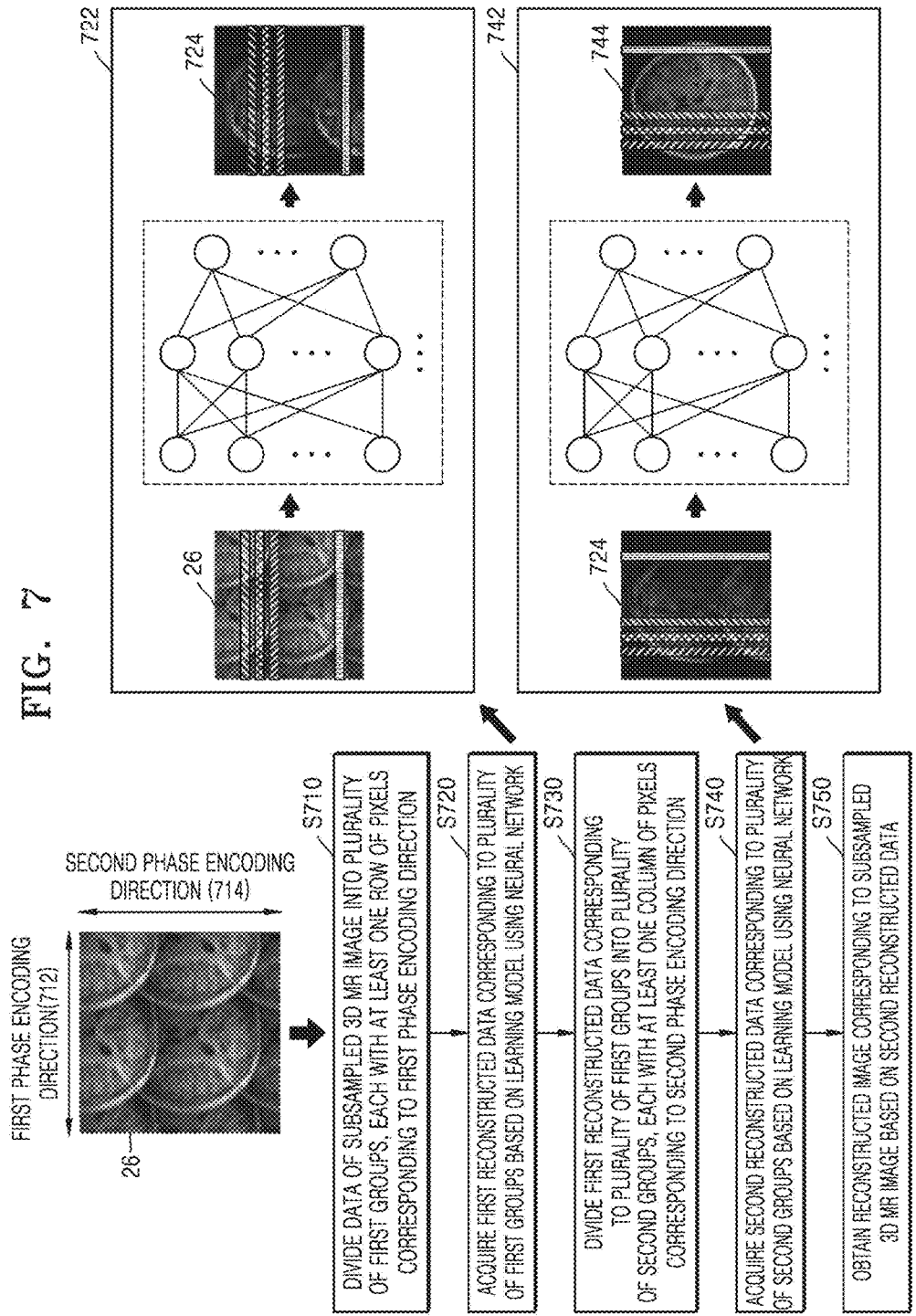
FIG. 7 illustrates a process of acquiring reconstructed data corresponding to a subsampled three-dimensional (3D) MR image based on a learning model using a neural network, according to an embodiment.

FIG. 7 illustrates a process of acquiring reconstructed data corresponding to a subsampled three-dimensional (3D) MR image 26 based on a learning model using a neural network (e.g., the neural network 40 of FIG. 4), according to an embodiment.

Referring to FIG. 7, the MRI apparatus 100 may acquire the subsampled 3D MR image 26 corresponding to input data. The subsampled 3D MR image 26 may contain aliasing artifacts that occur in two directions perpendicular to each other. Furthermore, the subsampled 3D MR image 26 may include first and second phase encoding directions 712 and 714. The first phase encoding direction 712 may be perpendicular to the second phase encoding direction 714. The subsampled 3D MR image 26 may include aliasing artifacts that occur in directions respectively corresponding to the first and second phase encoding directions 712 and 714.

In the case of the subsampled 3D MR image 26, it may be difficult to acquire reconstructed data due to a large amount of data to be reconstructed. Thus, according to embodiments, by sequentially acquiring reconstructed data in either of the first and second phase encoding directions 712 and 714 based on the learning model using the neural network 40, the MRI apparatus 100 may efficiently remove aliasing artifacts in the subsampled 3D MR image 26.

Referring to FIG. 7, the MRI apparatus 100 may divide data of the subsampled 3D MR image 26 into a plurality of first groups, each including at least one row of pixels corresponding to the first phase encoding direction 712 (S710). The method, performed by the MRI apparatus 100, of dividing the data of the subsampled 3D MR image 26 into the plurality of first groups may correspond to the grouping method for the data of the subsampled MR image 20 described with reference to FIGS. 3 and 4, and thus descriptions already provided above with respect to FIGS. 3 and 4 will be omitted here.

The MRI apparatus 100 may acquire first reconstructed data 724 corresponding to the plurality of first groups in the subsampled 3D MR image 26 based on the learning model using the neural network 40 (S720).

The MRI apparatus 100 may divide the first reconstructed data 724 corresponding to the plurality of first groups into a plurality of second groups, each including at least one column of pixels corresponding to the second phase encoding direction 714 (S730).

The method of dividing the first reconstructed data 724 corresponding to the plurality of first groups into the plurality of second groups may correspond to the grouping method for the data of the subsampled MR image 20 described with reference to FIGS. 3 and 4, and thus descriptions already provided above with respect to FIGS. 3 and 4 will be omitted here.

The MRI apparatus 100 may acquire, based on the learning model using the neural network 40, second reconstructed data 744 corresponding to the plurality of second groups in the first reconstructed data 724 corresponding to the plurality of first groups (S740).

View 722 illustrates acquiring the first reconstructed data 724 corresponding to the plurality of first groups in the subsampled 3D MR image 26, and view 742 illustrates acquiring the second reconstructed data 744 corresponding to the plurality of second groups in the first reconstructed data 724. Views 722 and 742 may correspond to the method of acquiring reconstructed data corresponding to the plurality of groups 322, 324, 326, . . . , and 328 in the subsampled MR image 20 as described above with reference to FIG. 3.

The MRI apparatus 100 may obtain a reconstructed image corresponding to the subsampled 3D MR image 26 based on the acquired second reconstructed data 744 (S750). The MRI apparatus 100 may obtain a reconstructed image corresponding to output data.

Although FIG. 7 illustrates an example in which the MRI apparatus 100 first acquires the first reconstructed data 724 with respect to the plurality of first groups corresponding to the first phase encoding direction 712 of the subsampled 3D MR image 26 and then the second reconstructed data 744 with respect to the plurality of second groups corresponding to the second phase encoding direction 714 of the first reconstructed data 724 corresponding to the plurality of first groups, embodiments are not limited thereto.

The MRI apparatus 100 may first acquire reconstructed data with respect to groups corresponding to a horizontal phase encoding direction and then reconstructed data with respect to groups corresponding to a vertical phase encoding direction based on the acquired reconstruction data. Alternatively, the MRI apparatus 100 may sequentially acquire reconstructed data with respect to groups corresponding to a vertical phase encoding direction and then reconstructed data with respect to groups corresponding to a horizontal phase encoding direction based on the acquired reconstruction data.

The order in which the MRI apparatus 100 acquires reconstructed data corresponding to a plurality of phase encoding directions of the subsampled 3D MR image 26 may be dynamically determined by the neural network 40 as an optimal method for obtaining the reconstructed image based on statistical machine learning results from the learning model using the neural network 40.

Figure 8:
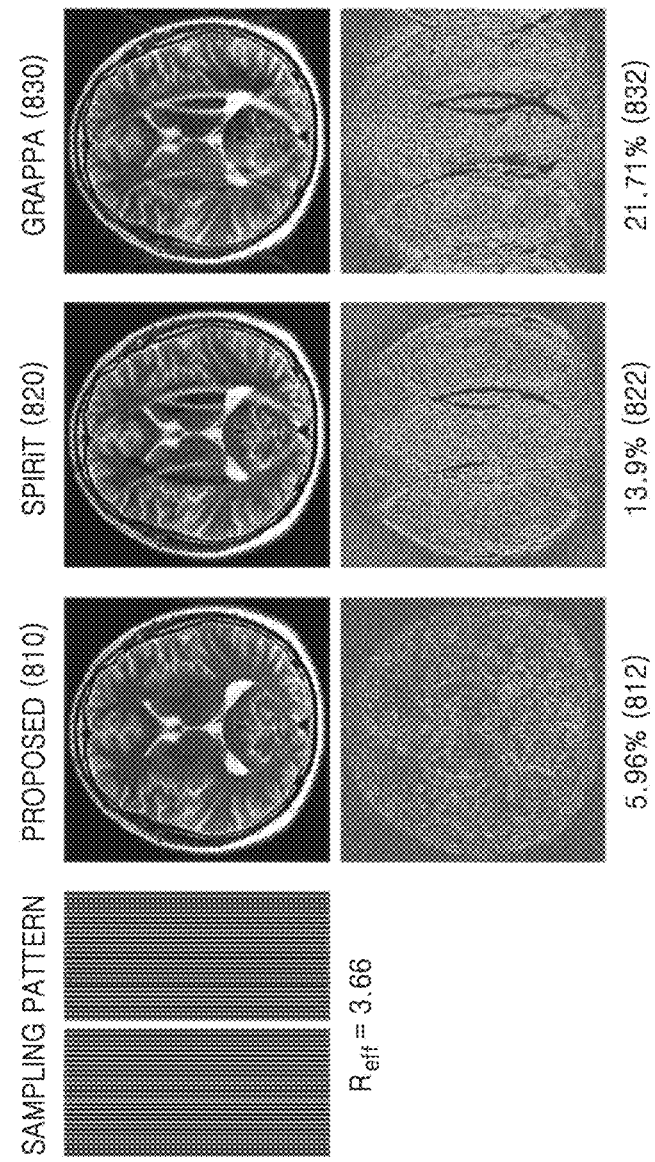
FIG. 8 illustrates experimental data on error rates of reconstructed images obtained.

FIG. 8 illustrates experimental data on error rates of reconstructed images obtained.

FIG. 8 illustrates results of experiments in which the MRI apparatus 100 reconstructs a subsampled MR image acquired at a reduction rate Reff of 3.66 by using a method proposed in the embodiments and conventional image acquisition acceleration algorithms.

Parameters used for the experiments include field of view (FOV) of 220*200 $mm^2$, matrix size of 384*216, slice thickness of 5 mm, 12-channel head coil, and repetition time (TR)/echo time (TE) of 5000/90 ms (fast spin echo T2-weighted brain image).

The MRI apparatus 100 may obtain a reconstructed image 810 by reconstructing, according to the method proposed in the embodiments, data of the subsampled MR image 20 in units of at least one row of pixels corresponding to a phase encoding direction based on a learning model using the neural network (40 of FIG. 4).

Furthermore, the MRI apparatus 100 may respectively obtain reconstructed images 820 and 830 corresponding to the subsampled MR image 20 by using Iterative Self-consistent Parallel Imaging Reconstruction From Arbitrary k-Space (SPIRiT) and GeneRalized Autocalibrating Partial Parallel Acquisition (GRAPPA) that are conventional image acquisition acceleration algorithms using parallel imaging.

In addition, the MRI apparatus 100 may acquire difference images 812, 822, and 832 respectively representing differences between each of the reconstructed images 810, 820, and 830 and an MR image obtained at the Nyquist sampling rate. The MRI apparatus 100 may calculate error rates between each of the reconstructed images 810, 820, and 830 and the MR image obtained at the Nyquist sampling rate.

The results of the experiments show that the MRI apparatus 100 may obtain the relatively accurate reconstructed image 810 with an error rate of 5.96% by using the proposed method according to the embodiments.

Figure 9:
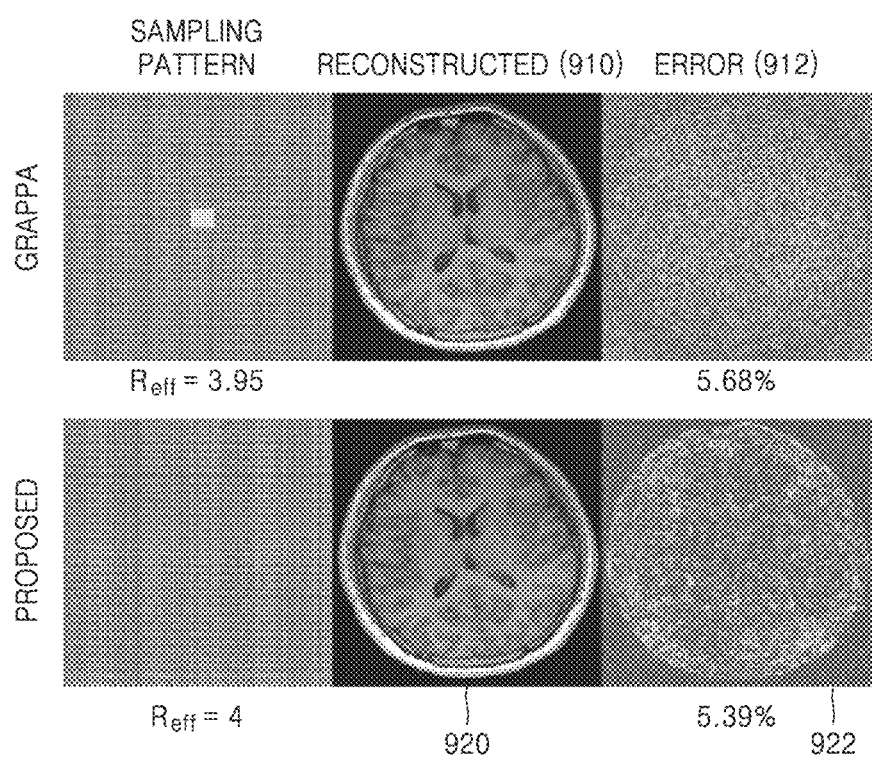
FIG. 9 illustrates other experimental data on error rates of reconstructed images.

FIG. 9 illustrates other experimental data on error rates of reconstructed images obtained.

FIG. 9 illustrates a result of an experiment in which the MRI apparatus 100 reconstructs a subsampled 3D MR image acquired at a reduction rate $R_{\textit{eff}}$ of 3.95 by using GRAPPA that is one from among conventional image acquisition acceleration algorithms and a result of an experiment in which the MRI apparatus 100 reconstructs a subsampled 3D MR image acquired at a reduction rate $R_{\textit{eff}}$ of 4 by using a proposed method according to embodiments.

Parameters used for the experiments are matrix size of 256*208*404, 12-channel head coil, and TR/TE/inversion time (TI) of 1800/2.52/900 ms (magnetization-prepared rapid gradient echo (MPRAGE) T1-weighted brain image).

According to the method proposed in the embodiments, the MRI apparatus 100 may obtain a reconstructed image 920 by sequentially reconstructing data of the subsampled 3D MR image in units of at least one row of pixels corresponding to a first phase encoding direction and in units of at least one column of pixels corresponding to a second phase encoding direction based on a learning model using the neural network (40 of FIG. 7).

Furthermore, the MRI apparatus 100 may obtain a reconstructed image 910 corresponding to the subsampled 3D MR image by using GRAPPA that is a conventional image acquisition acceleration algorithm using parallel imaging.

In addition, the MRI apparatus 100 may acquire difference images 912 and 922 respectively representing differences between either of the reconstructed images 910 and 920 and an MR image obtained at the Nyquist sampling rate. The MRI apparatus 100 may calculate error rates between either of the reconstructed images 910 and 920 and the MR image obtained at the Nyquist sampling rate.

The results of the experiments show that the MRI apparatus 100 may obtain the more accurate reconstructed image 920 corresponding to the subsampled 3D MR image when using the proposed method according to the embodiments than when using GRAPPA even though the subsampled 3D MR image for the reconstructed image 920 is acquired at the reduction rate $R_{\textit{eff}}$ of 4 that is higher than that for the subsampled 3D MR image reconstructed using GRAPPA.

Figure 10:
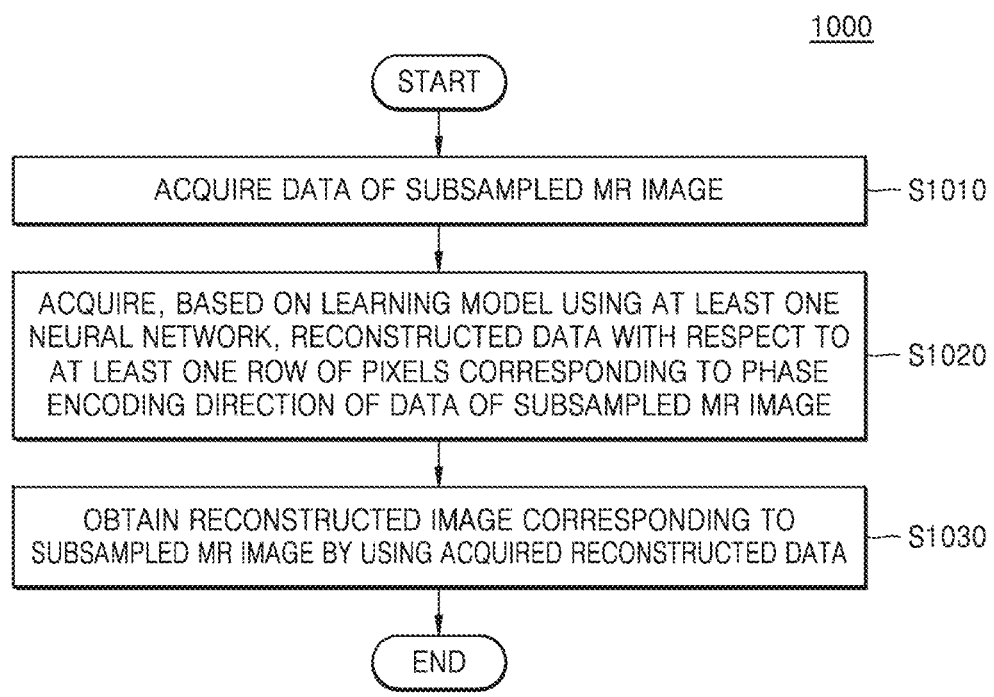
FIG. 10 is a flowchart of a method of obtaining a reconstructed image corresponding to a subsampled MR image based on a learning model using a neural network, according to an embodiment.

FIG. 10 is a flowchart of a method 1000 of obtaining the reconstructed image 80 (of FIG. 3) corresponding to the subsampled MR image 20 (of FIG. 3) based on a learning model using the neural network 40 (of FIG. 3), according to an embodiment.

The method 1000 of FIG. 10 may be performed by the MRI apparatus (100 of FIG. 2) having the above-described configuration.

The MRI apparatus 100 acquires data of the subsampled MR image 20 (S1010). The subsampled MR image 20 may be an image corresponding to input data provided to the MRI apparatus 100 to obtain the reconstructed image 80.

The MRI apparatus 100 acquires, based on a learning model using at least one neural network 40, reconstructed data with respect to at least one row of pixels corresponding to a phase encoding direction of the data of the subsampled MR image 20 (S1020).

According to an embodiment, the MRI apparatus 100 may divide the data of the subsampled MR image 20 into a plurality of groups, each including at least one row of pixels corresponding to a phase encoding direction. Furthermore, the MRI apparatus 100 may acquire pieces of reconstructed data respectively corresponding to the plurality of groups based on the learning model using the at least one neural network 40. The MRI apparatus 100 obtains the reconstructed image 80 corresponding to the subsampled MR image 20 based on the acquired pieces of reconstructed data (S1030). The reconstructed image 80 may be an image corresponding to output data acquired when the subsampled MR image 20 corresponding to input data is input to the MRI apparatus 100.

Figure 11:
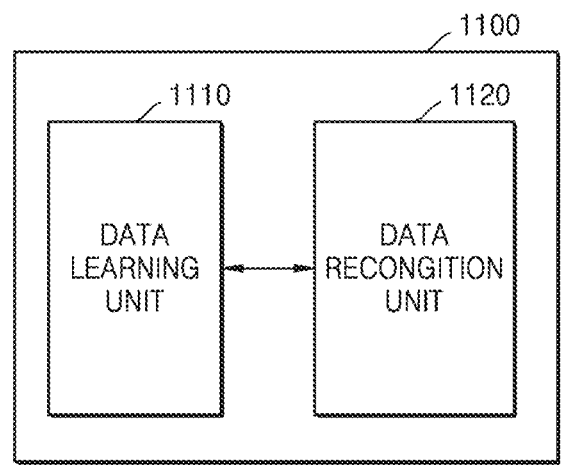
FIG. 11 is a block diagram of a processor according to an embodiment.

FIG. 11 is a block diagram of a processor 1100 according to an embodiment.

Referring to FIG. 11, according to embodiments, the processor 1100 may include a data learning unit 1110 and a data recognition unit 1120. The processor 1100 may correspond to the processor 120 described with reference to FIG. 2. Furthermore, the processor 1100 may correspond to one or a combination of the image processor 11 and the controller 30 that will be described below with reference to FIG. 14.

The data learning unit 1110 may learn criteria for acquiring reconstructed data corresponding to the subsampled MR image 20. The data learning unit 1110 may learn criteria with respect to which data will be used to acquire reconstructed data corresponding to the subsampled MR image 20 and how the reconstructed data will be acquired using the data. The data learning unit 1110 may learn criteria for acquiring reconstructed data corresponding to the subsampled MR image 20 by acquiring data to be used for learning and applying the acquired data to a data recognition model that will be described below.

The data recognition unit 1120 may acquire reconstructed data based on data. The data recognition unit 1120 may acquire reconstructed data from predetermined data by using a trained data recognition model. The data recognition unit 1120 may acquire the reconstructed data based on the predetermined data by acquiring the predetermined data according to preset criteria obtained by training and using the data recognition model that takes the acquired data as an input value. Furthermore, a resultant value output by the data recognition model that takes the acquired data as an input value may be used to refine the data recognition model.

At least one of the data learning unit 1110 and the data recognition unit 1120 may be fabricated in the form of at least one hardware chip that may be mounted in the MRI apparatus 100. For example, the at least one of the data learning unit 1110 and the data recognition unit 1120 may be manufactured in the form of a dedicated hardware chip for artificial intelligence (AI), or as part of a conventional general-purpose processor (e.g., a central processing unit (CPU) or application processor) or dedicated graphics processor (e.g., a graphical processing unit (GPU)) and be mounted in the MRI apparatus 100.

In this case, the data learning unit 1110 and the data recognition unit 1120 may be mounted in one MRI apparatus 100, or be mounted respectively in the MRI apparatus 100 and an external device. For example, one of the data learning unit 1110 and the data recognition unit 1120 may be included in the MRI apparatus 100 while the other may be included in a server. Furthermore, model information created by the data learning unit 1110 may be provided to the data recognition unit 1120 by wire or wirelessly, and data input to the data recognition unit 1120 may be provided to the data learning unit 1110 as additional training data.

In addition, at least one of the data learning unit 1110 and the data recognition unit 1120 may be implemented as a software module. When the at least one of the data learning unit 1110 and the data recognition unit 1120 is implemented as a software module (or a program module including instructions), the software module may be stored in non-transitory computer readable recording media. Furthermore, in this case, at least one software module may be provided by an operating system (OS) or predetermined application. Alternatively, some of the at least one software module may be provided by the OS while the other ones may be provided by the predetermined application.

Figure 12:
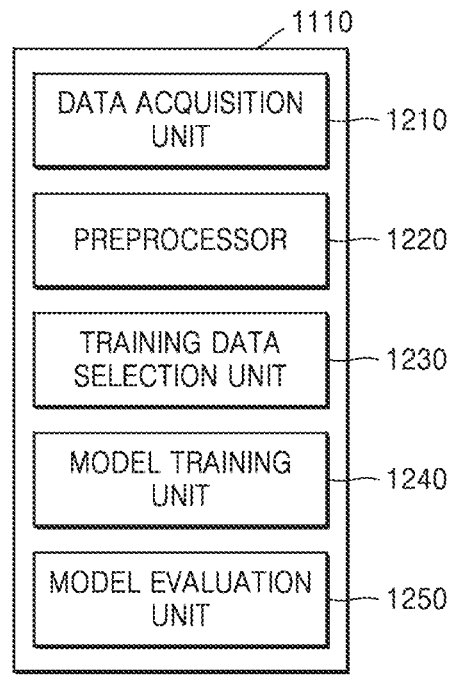
FIG. 12 is a block diagram of a data learning unit according to an embodiment.

FIG. 12 is a block diagram of the data learning unit 1110 according to an embodiment.

Referring to FIG. 12, according to embodiments, the data learning unit 1110 may include a data acquisition unit 1210, a preprocessor 1220, a training data selection unit 1230, a model training unit 1240, and a model evaluation unit 1250.

The data acquisition unit 1210 may acquire data for acquiring reconstructed data corresponding to the subsampled MR image (20 of FIG. 3). The data acquisition unit 1210 may acquire data for learning for acquisition of reconstructed data. The data for the learning for acquisition of the reconstructed data may include data of the subsampled MR image 20.

According to an embodiment, the data acquisition unit 1210 may acquire data of the subsampled MR image 20 by subsampling MR signals obtained via an RF coil. The data acquisition unit 1210 may acquire the data of the subsampled MR image 20 by subsampling the obtained MR signals in a regular or irregular pattern.

Furthermore, the data acquisition unit 1210 may acquire data of the subsampled 3D MR image (26 of FIG. 7) by subsampling MR signals obtained via an RF coil in two phase encoding directions that are perpendicular to each other.

In this case, the RF coil may include a multi-coil RF coil, and the data acquisition unit 1210 may further acquire sensitivity information of the multi-channel RF coil. Furthermore, the data acquisition unit 1210 may acquire data of a plurality of subsampled MR images 20 respectively obtained via the multi-channel RF coil.

According to another embodiment, the data acquisition unit 1210 may acquire data of the subsampled MR image 20 from at least one of an external MRI apparatus, an external server, and a database.

The subsampled MR image 20 may include aliasing artifacts that occur in a direction corresponding to a phase encoding direction. The subsampled MR image 20 may include aliasing artifacts that occur in a direction parallel to the phase encoding direction.

The data acquisition unit 1210 may acquire the real image data (22 of FIG. 5) and the imaginary image data (24 of FIG. 5) corresponding to the subsampled MR image 20. Data of the subsampled MR image 20 may be complex data. The data acquisition unit 1210 may separate complex data corresponding to the subsampled MR image 20 into real and imaginary parts in a Cartesian coordinate format to thereby acquire the real image data 22 and the imaginary image data 24.

Furthermore, the data acquisition unit 1210 may acquire magnitude image data and phase image data corresponding to the subsampled MR image 20. The data acquisition unit 1210 may separate complex data into a magnitude and a phase in a polar coordinate format to thereby acquire the magnitude image data and phase image data.

The preprocessor 1220 may preprocess the acquired data such that the acquired data may be used for learning for acquisition of reconstructed data. The preprocessor 1220 may process the acquired data into a preset format such that the model training unit 1240 to be described later may use the acquired data for learning that is performed for acquisition of reconstructed data.

The preprocessor 1220 may divide the data of the subsampled MR image 20 into a plurality of groups, each including at least one row of pixels corresponding to a phase encoding direction. The preprocessor 1220 may divide the data of the subsampled MR image 20 into a plurality of groups, each including at least one row of pixels parallel to the phase encoding direction. The method, performed by the preprocessor 1220, of dividing the data of the subsampled MR image 20 into the plurality of groups may correspond to the grouping method described with reference to FIGS. 3 and 4.

The preprocessor 1220 may divide the real image data 22 corresponding to the subsampled MR image 20 into a plurality of groups, each including at least one row of pixels corresponding to the phase encoding direction. Furthermore, the preprocessor 1220 may divide the imaginary image data 24 corresponding to the subsampled MR image 20 into a plurality of groups, each including at least one row of pixels corresponding to the phase encoding direction. The grouping methods for the real image data 22 and the imaginary image data 24 may correspond to the grouping method for the data of the subsampled MR image 20 described above with reference t to FIGS. 3 and 4.

The preprocessor 1220 may divide data of the subsampled 3D MR image 26 into a plurality of first groups, each including at least one row of pixels corresponding to a first phase encoding direction. Furthermore, the preprocessor 1220 may divide first reconstructed data corresponding to the plurality of first groups into a plurality of second groups, each including at least one column of pixels corresponding to a second phase encoding direction. The first phase encoding direction may be perpendicular to the second phase encoding direction.

The training data selection unit 1230 may select data for learning from among the preprocessed data. The selected data may be provided to the model training unit 1240. The training data selection unit 1230 may select data for learning from among the preprocessed data according to preset criteria for acquisition of reconstructed data. Furthermore, the training data selection unit 1230 may select data according to preset criteria learned by the model training unit 1240 to be described later.

The training data selection unit 1230 may select one of a plurality of groups in the subsampled MR image 20 and provide the selected group to the model training unit 1240. To acquire pieces of reconstructed data respectively corresponding to the plurality of groups in the subsampled MR image 20, the training data selection unit 1230 may select at least one of the plurality of groups in a predetermined order and provide the selected group to the model training unit 1240.

The model training unit 1240 may learn criteria with respect to how reconstructed data corresponding to the subsampled MR image 20 will be acquired based on training data and how the reconstructed image (80 of FIG. 3) corresponding to the subsampled MR image 20 will be obtained based on the acquired reconstructed data. Furthermore, the model training unit 1240 may learn a criterion with respect to which training data is to be used for acquisition of reconstructed data.

In addition, the model training unit 1240 may acquire reconstructed data corresponding to the subsampled MR image 20 and use training data to train a data recognition model that is used for obtaining the reconstructed image 80 based on the acquired reconstructed data. In this case, the data recognition model may be a previously created model. For example, the data recognition model may be a model previously created by receiving basic training data (e.g., a subsampled MR image of a sample, etc.) as input.

The data recognition model may be created by taking into account an application field of the data recognition model, an objective of learning, or a computer performance of a device. For example, the data recognition model may be a model based on a neural network. Models such as DNN, RNN, BRDNN, MLP, and CNN may be used as the data recognition model, but embodiments are not limited thereto.

According to embodiments, when a plurality of data recognition models are previously created, the model training unit 1240 may determine a data recognition model having a high correlation between input training data and basic training data as a data recognition model to be trained. In this case, the basic training data may be pre-classified according to the type of data, and the data recognition model may be previously created for each data type. For example, the basic training data may be pre-classified based on various criteria such as an area where the training data is generated, a time at which the training data is generated, a size of the training data, a genre of the training data, a creator of the training data, the type of an object in the training data, etc.

Furthermore, for example, the model training unit 1240 may train a data recognition model by using a learning algorithm including error back-propagation or gradient descent.

As another example, the model training unit 1240 may use supervised learning that takes training data as an input value to train a data recognition model. Furthermore, by learning the type of data for acquiring reconstructed data corresponding to the subsampled MR image 20 on its own without separate guidance, the model training unit 1240 may train the data recognition model by using unsupervised learning that finds criteria for acquiring reconstructed data. In addition, the model training unit 1240 may train the data recognition model by using reinforcement learning that uses a feedback regarding whether the result of reconstructed data acquired according to learning is correct.

Furthermore, after the data recognition model is trained, the model training unit 1240 may store the trained data recognition model. In this case, the model training unit 1240 may store the trained data recognition model in a memory of the MRI apparatus 100 including the data recognition unit (1120 of FIG. 11). Alternatively, the model training unit 1240 may store the trained data recognition model in a memory of the MRI apparatus 100 including the data recognition unit 1120 of FIG. 13 that will be described below. Alternatively, the model training unit 1240 may store the trained data recognition model in a memory of a server connected by wire or wirelessly to the MRI apparatus 100.

In this case, for example, the memory in which the trained data recognition model may store together an instruction or data related to at least one component of the MRI apparatus 100. Furthermore, the memory may also store software and/or programs. For example, the programs may include kernel, middleware, application programming interface (API) and/or application program (or "application").

The model evaluation unit 1250 inputs evaluation data to the data recognition model, and may cause the model training unit 1240 to learn again when a recognition result obtained from the evaluation data does not satisfy a predetermined criterion. In this case, the evaluation data may be preset data for evaluating the data recognition model. Here, the evaluation data may include a matching ratio between a reconstructed image obtained based on the data recognition model and an MR image obtained according to a sampling rate higher than the Nyquist sampling rate.

For example, when the number or ratio of pieces of evaluation data with respect to which recognition results are not accurate from among recognition results output from the trained data recognition model with respect to evaluation data exceeds a preset threshold, the model training unit 1250 may evaluate that a predetermined criterion is not satisfied. For example, when the predetermined criterion is defined as a ratio of 2%, and when the trained data recognition model outputs wrong recognition results with respect to more than 20 pieces of evaluation data among a total of 1000 pieces of evaluation data, the model evaluation unit 1250 may evaluate the trained data recognition model as not being suitable.

Furthermore, when a plurality of trained data recognition model are stored, the model evaluation unit 1250 may evaluate whether each of the plurality of trained data recognition model satisfies a predetermined criterion, and determine a trained data recognition model satisfying the predetermined criterion as a final data recognition model. In this case, when a plurality of trained data recognition model satisfy the predetermined criterion, the model evaluation unit 1250 may determine one or a predetermined number of data recognition models that are preset in order from highest to lowest evaluation scores as being a final data recognition model.

In addition, at least one of the data acquisition unit 1210, the preprocessor 1220, the training data selection unit 1230, the model training unit 1240, and the model evaluation unit 1250 included in the data learning unit 1110 may be fabricated in the form of at least one hardware chip that may be mounted in the MRI apparatus 100. For example, the at least one of the data acquisition unit 1210, the preprocessor 1220, the training data selection unit 1230, the model training unit 1240, and the model evaluation unit 1250 may be manufactured in the form of a dedicated hardware chip for AI, or as part of a conventional general-purpose processor (e.g., a CPU or application processor) or dedicated graphics processor (e.g., a GPU) and be mounted in the MRI apparatus 100.

Furthermore, the data acquisition unit 1210, the preprocessor 1220, the training data selection unit 1230, the model training unit 1240, and the model evaluation unit 1250 may be mounted in one MRI apparatus 100, or be mounted respectively in the MRI apparatus 100 and an external device. For example, some of the data acquisition unit 1210, the preprocessor 1220, the training data selection unit 1230, the model training unit 1240, and the model evaluation unit 1250 may be included in the MRI apparatus 100 while the rest thereof may be included in a server.

Furthermore, at least one of the data acquisition unit 1210, the preprocessor 1220, the training data selection unit 1230, the model training unit 1240, and the model evaluation unit 1250 may be implemented as a software module. When the at least one of the data acquisition unit 1210, the preprocessor 1220, the training data selection unit 1230, the model training unit 1240, and the model evaluation unit 1250 is implemented as a software module (or a program module including instructions), the software module may be stored in non-transitory computer readable recording media. Furthermore, in this case, at least one software module may be provided by an OS or predetermined application. Alternatively, some of the at least one software module may be provided by the OS while the other ones may be provided by the predetermined application.

Figure 13:
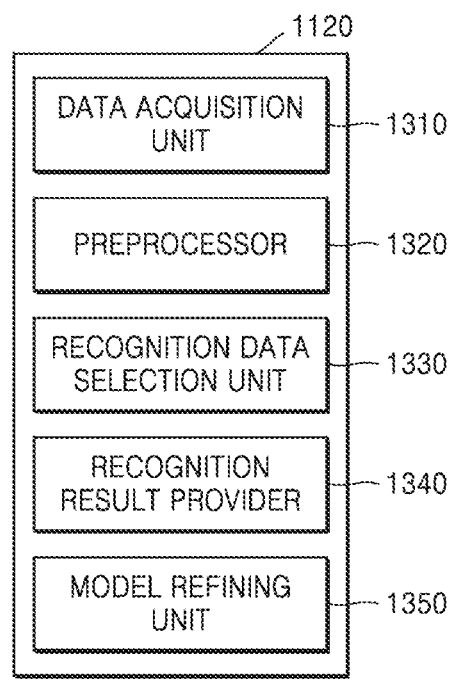
FIG. 13 is a block diagram of a data recognition unit according to an embodiment.

FIG. 13 is a block diagram of the data recognition unit 1120 according to an embodiment.

Referring to FIG. 13, according to embodiments, the data recognition unit 1120 may include a data acquisition unit 1310, a preprocessor 1320, a recognition data selection unit 1330, a recognition result provider 1340, and a model refining unit 1350.

The data acquisition unit 1310 may acquire data for acquiring reconstructed data corresponding to the subsampled MR image (20 of FIG. 3). The preprocessor 1320 may preprocess the acquired data such that the acquired data may be used for acquisition of reconstructed data. The preprocessor 1320 may process the acquired data into a preset format such that the recognition result provider 1340 to be described below may use the acquired data for acquiring reconstructed data corresponding to the subsampled MR image 20.

The recognition data selection unit 1330 may select data for acquiring reconstructed data from among the preprocessed data. The selected data may be provided to the recognition result provider 1340. The recognition data selection unit 1330 may select some or all of the preprocessed data according to preset criteria for acquisition of reconstructed data. Furthermore, the recognition data selection unit 1330 may select data according to preset criteria learned by the model training unit (1240 of FIG. 12).

The recognition result provider 1340 may acquire reconstructed data corresponding to the subsampled MR image 20 by applying the selected data to a data recognition model. Furthermore, the recognition result provider 1340 may use the acquired reconstructed data to obtain the reconstructed image (80 of FIG. 3) corresponding to the subsampled MR image 20. The recognition result provider 1340 may provide a recognition result according to the purpose of data recognition. By using the data selected by the recognition data selection unit 1330 as an input value, the recognition result provider 1340 may apply the selected data to a data recognition model. Furthermore, the recognition result may be determined by the data recognition model.

The reconstructed data provided by the recognition result provider 1340 may include parameters or weight values used to acquire data of the reconstructed image 80 based on the data of the subsampled MR image 20. Furthermore, the recognition result provider 1340 may provide the reconstructed image 80 by applying to the data of the subsampled MR image 20 the reconstructed data including parameters or weight values for acquiring the data of the reconstructed image 80 based on the data of the subsampled MR image 20.

The model refining unit 1350 may use and refine a data recognition model based on evaluation of the recognition result provided by the recognition result provider 1340. For example, the model refining unit 1350 may cause the model training unit 1240 to use and refine the data recognition model by providing the recognition result from the recognition result provider 1340 to the model learning unit 1240.

In addition, at least one of the data acquisition unit 1310, the preprocessor 1320, the recognition data selection unit 1330, the recognition result provider 1340, and the model refining unit 1350 included in the data recognition unit 1320 may be fabricated in the form of at least one hardware chip that may be mounted in the MRI apparatus 100. For example, the at least one of the data acquisition unit 1310, the preprocessor 1320, the recognition data selection unit 1330, the recognition result provider 1340, and the model refining unit 1350 may be manufactured in the form of a dedicated hardware chip for AI, or as part of a conventional general-purpose processor (e.g., a CPU or application processor) or dedicated graphics processor (e.g., a GPU) and be mounted in the MRI apparatus 100.

Furthermore, the data acquisition unit 1310, the preprocessor 1320, the recognition data selection unit 1330, the recognition result provider 1340, and the model refining unit 1350 may be mounted in one MRI apparatus 100, or be mounted respectively in the MRI apparatus 100 and an external device. For example, some of the data acquisition unit 1310, the preprocessor 1320, the recognition data selection unit 1330, the recognition result provider 1340, and the model refining unit 1350 may be included in the MRI apparatus 100 while the rest thereof may be included in a server.

Furthermore, at least one of the data acquisition unit 1310, the preprocessor 1320, the recognition data selection unit 1330, the recognition result provider 1340, and the model refining unit 1350 may be implemented as a software module. When the at least one of the data acquisition unit 1210, the preprocessor 1220, the training data selection unit 1230, the model training unit 1240, and the model evaluation unit 1250 is implemented as a software module (or a program module including instructions), the software module may be stored in non-transitory computer readable recording media. Furthermore, in this case, at least one software module may be provided by an OS or predetermined application. Alternatively, some of the at least one software module may be provided by the OS while the other ones may be provided by the predetermined application.

Figure 14:
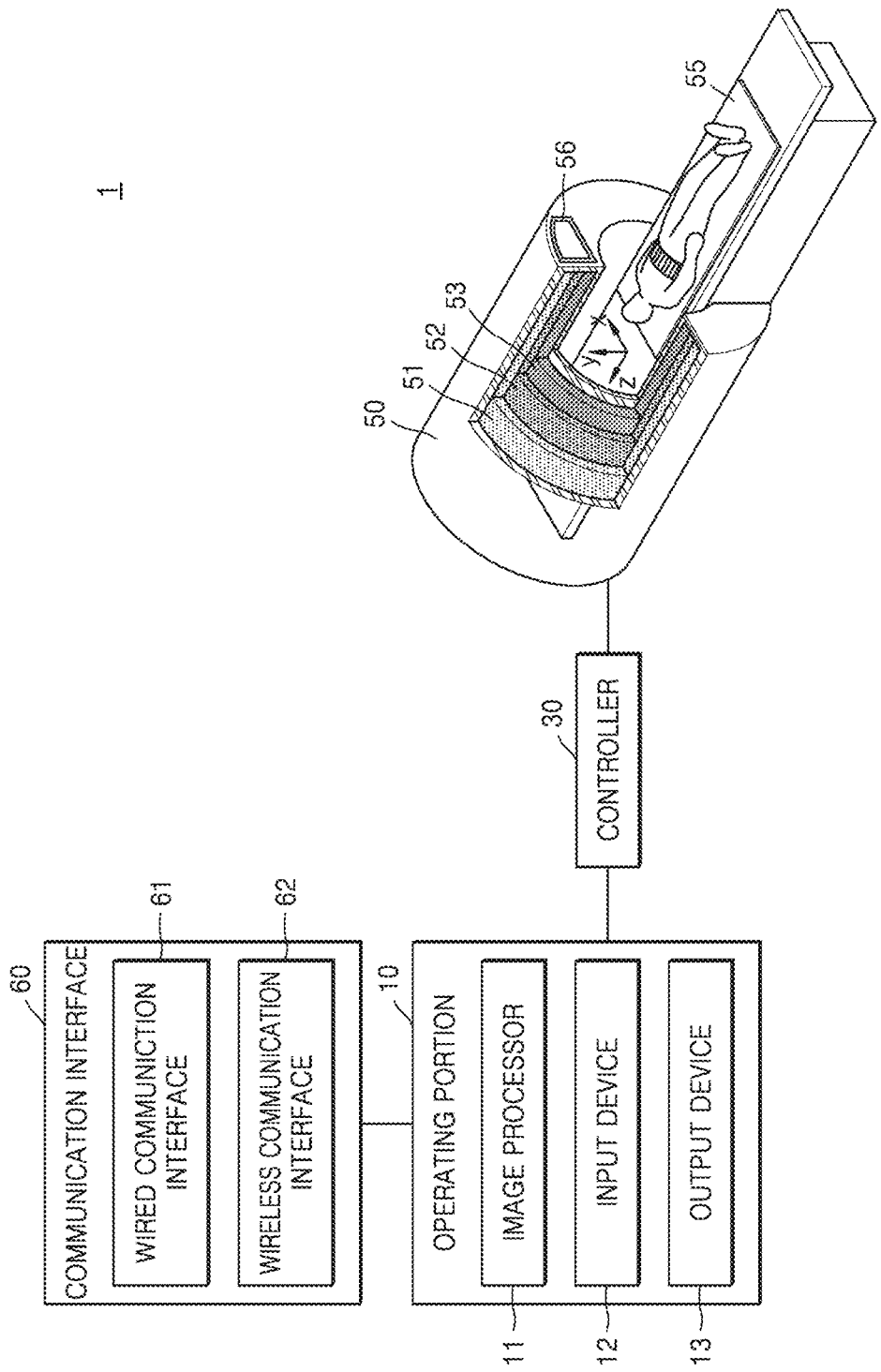
FIG. 14 is a schematic diagram of an MRI system according to an embodiment.

FIG. 14 is a schematic diagram of an MRI system 1 according to an embodiment.

Referring to FIG. 14, the MRI system 1 may include an operating portion 10, a controller 30, and a scanner 50. The controller 30 may be independently separated from the operating portion 10 and the scanner 50. Furthermore, the controller 30 may be separated into a plurality of subcomponents and incorporated into the operating portion 10 and the scanner 50 in the MRI system 1. Operations of the components in the MRI system 1 will now be described in detail.

The scanner 50 may be formed to have a cylindrical shape (e.g., a shape of a bore) having an empty inner space into which an object may be inserted. A static magnetic field and a gradient magnetic field are created in the inner space of the scanner 50, and an RF signal is emitted toward the inner space.

The scanner 50 may include a static magnetic field generator 51, a gradient magnetic field generator 52, an RF coil unit 53, a table 55, and a display 56. The static magnetic field generator 51 creates a static magnetic field for aligning magnetic dipole moments of atomic nuclei of the object in a direction of the static magnetic field. The static magnetic field generator 51 may be formed as a permanent magnet or superconducting magnet using a cooling coil.

The gradient magnetic field generator 52 is connected to the controller 30 and generates a gradient magnetic field by applying a gradient to a static magnetic field in response to a control signal received from the controller 30. The gradient magnetic field generator 52 includes X, Y, and Z coils for generating gradient magnetic fields in X-, Y-, and Z-axis directions crossing each other at right angles and generates a gradient signal according to a position of a region being imaged to differently induce resonance frequencies according to regions of the object.

The RF coil unit 53 connected to the controller 30 may emit an RF signal toward the object in response to a control signal received from the controller 30 and receive an MR signal emitted from the object. In detail, the RF coil unit 53 may transmit, toward atomic nuclei of the object having precessional motion, an RF signal having the same frequency as that of the precessional motion, stop transmitting the RF signal, and then receive an MR signal emitted from the object.

The RF coil unit 53 may be formed as a transmitting RF coil for generating an electromagnetic wave having an RF corresponding to the type of an atomic nucleus, a receiving RF coil for receiving an electromagnetic wave emitted from an atomic nucleus, or one transmitting/receiving RF coil serving both functions of the transmitting RF coil and receiving RF coil. Furthermore, in addition to the RF coil unit 53, a separate coil may be attached to the object. Examples of the separate coil may include a head coil, a spine coil, a torso coil, and a knee coil according to a region being imaged or to which the separate coil is attached.

The display 56 may be disposed outside and/or inside the scanner 50. The display 56 is also controlled by the controller 30 to provide a user or the object with information related to medical imaging.

Furthermore, the scanner 50 may include an object monitoring information acquisition unit configured to acquire and transmit monitoring information about a state of the object. For example, the object monitoring information acquisition unit may acquire monitoring information related to the object from a camera for capturing images of a movement or position of the object, a respiration measurer for measuring the respiration of the object, an ECG measurer for measuring the electrical activity of the heart, or a temperature measurer for measuring a temperature of the object and transmit the acquired monitoring information to the controller 30. The controller 30 may in turn control an operation of the scanner 50 based on the monitoring information. Operations of the controller 30 will now be described in more detail.

The controller 30 may control overall operations of the scanner 50.

The controller 30 may control a sequence of signals formed in the scanner 50. The controller 30 may control the gradient magnetic field generator 52 and the RF coil unit 53 according to a pulse sequence received from the operating portion 10 or a designed pulse sequence.

A pulse sequence may include all pieces of information used to control the gradient magnetic field generator 52 and the RF coil unit 53. For example, the pulse sequence may include information about a strength, a duration, and application timing of a pulse signal applied to the gradient magnetic field generator 52.

The controller 30 may control a waveform generator for generating a gradient wave, i.e., an electrical pulse according to a pulse sequence and a gradient amplifier for amplifying the generated electrical pulse and transmitting the same to the gradient magnetic field generator 52. Thus, the controller 30 may control formation of a gradient magnetic field by the gradient magnetic field generator 52.

Furthermore, the controller 30 may control an operation of the RF coil unit 53. For example, the controller 30 may supply an RF pulse having a resonance frequency to the RF coil unit 30 that emits an RF signal toward the object, and receive an MR signal received by the RF control unit 53. In this case, the controller 30 may adjust emission of an RF signal and reception of an MR signal according to an operating mode by controlling an operation of a switch (e.g., a T/R switch) for adjusting transmitting and receiving directions of the RF signal and the MR signal based on a control signal.

The controller 30 may control a movement of the table 55 where the object is placed. Before MRI is performed, the controller 30 may move the table 55 according to which region of the object is to be imaged.

The controller 30 may also control the display 56. For example, the controller 30 control the on/off state of the display 56 or a screen to be output on the display 56 according to a control signal.

The controller 30 may be formed as an algorithm for controlling operations of the components in the MRI system 1, a memory for storing data in the form of a program, and a processor for performing the above-described operations by using the data stored in the memory. In this case, the memory and the processor may be implemented as separate chips. Alternatively, the memory and processor may be incorporated into a single chip.

The operating portion 10 may control overall operations of the MRI system 1 and include an image processor 11, an input device 12, and an output device 13.

The image processor 11 may control the memory to store an MR signal received from the controller 30, and generate image data with respect to the object from the stored MR signal by applying an image reconstruction technique by using an image processor.

For example, when a k space (for example, also referred to as a Fourier space or a frequency space) of the memory is filled with digital data to complete k-space data, the image processor 11 may reconstruct image data from the k-space data by applying various image reconstruction techniques (e.g., by performing inverse Fourier transform on the k-space data) by using the image processor.

Furthermore, the image processor 11 may perform various signal processing operations on MR signals in parallel. For example, image processing unit 11 may perform signal processing on a plurality of MR signals received via a multi-channel RF coil in parallel to convert the plurality MR signals into image data. In addition, the image processor 11 may store not only the image data in the memory, or the controller 30 may store the same in an external server via a communication unit 60 as will be described below.

The input device 12 may receive, from the user, a control instruction for controlling the overall operations of the MRI system 1. For example, the input device 12 may receive, from the user, object information, parameter information, a scan condition, and information about a pulse sequence. The input device 12 may be a keyboard, a mouse, a track ball, a voice recognizer, a gesture recognizer, a touch screen, or any other input device.

The output device 13 may output image data generated by the image processor 11. The output device 13 may also output a user interface (UI) configured so that the user may input a control instruction related to the MRI system 1. The output device 13 may be formed as a speaker, a printer, a display, or any other output device.

Furthermore, although FIG. 14 shows that the operating portion 10 and the controller 30 are separate components, the operating portion 10 and the controller 30 may be included in a single device as described above. Furthermore, processes respectively performed by the operating portion 10 and the controller 30 may be performed by another component. For example, the image processor 11 may convert an MR signal received from the controller 30 into a digital signal, or the controller 30 may directly perform the conversion of the MR signal into the digital signal.

The MRI system 1 may further include a communication interface 60 and be connected to an external device such as a server, a medical apparatus, and a portable device (e.g., a smartphone, a tablet PC, a wearable device, etc.) via the communication interface 60.

The communication interface 60 may include at least one component that enables communication with an external device. For example, the communication interface 60 may include at least one of a local area communication module, a wired communication interface 61, and a wireless communication interface 62.

The communication interface 60 may receive a control signal and data from an external device and transmit the received control signal to the controller 30 so that the controller 30 may control the MRI system 1 according to the received signal.

Alternatively, by transmitting a control signal to an external device via the communication interface 60, the controller 30 may control the external device according to the control signal.

For example, the external device may process data of the external device according to a control signal received from the controller 30 via the communication interface 60.

A program for controlling the MRI system 1 may be installed on the external device and may include instructions for performing some or all of the operations of the controller 30.

The program may be preinstalled on the external device, or a user of the external device may download the program from a server providing an application for installation. The server providing an application may include a recording medium having the program recorded thereon.

Embodiments may be implemented through non-transitory computer-readable recording media having recorded thereon computer-executable instructions and data. The instructions may be stored in the form of program codes, and when executed by a processor, generate a predetermined program module to perform an operation. Furthermore, when being executed by the processor, the instructions may perform operations according to the embodiments.

Furthermore, embodiments may be implemented as a computer program including instructions that may be executed by a computer, or a computer program product.

While embodiments have been described with reference to the figures, it will be understood by those of ordinary skill in the art that various changes in form and details may be made therein without departing from the spirit and scope of the disclosure as defined by the following claims. Accordingly, the above embodiments and all aspects thereof are examples only and are not limiting.

What is claimed is:

1. A magnetic resonance imaging (MRI) apparatus comprising:
   a processor; and
   a memory storing at least one program comprising instructions that, when executed by the processor, cause the processor to:
   acquire data of at least one subsampled magnetic resonance (MR) image and data of at least one fully sampled MR image;
   obtain a learning model using at least one neural network by learning correlations between the at least one subsampled MR image and the at least one fully sampled MR image in units of at least one row of pixels corresponding to a phase encoding direction;
   acquire data of a subsampled MR image;
   divide the data of the subsampled MR image into a plurality of groups, each corresponding to the at least one row of pixels corresponding to the phase encoding direction;
   acquire, based on the learning model using the at least one neural network, reconstructed data respectively corresponding to the plurality of groups with respect to the at least one row of pixels corresponding to the phase encoding direction of the data of the subsampled MR image; and
   obtain a reconstructed image corresponding to the subsampled MR image, using the acquired reconstructed data.

2. The MRI apparatus of claim 1, wherein the memory stores the at least one program comprising the instructions that, when executed by the processor, further cause the processor to:
   acquire subsampled real image data and subsampled imaginary image data;
   divide the subsampled real image data and the subsampled imaginary image data into the plurality of groups, each corresponding to the at least one row of pixels corresponding to the phase encoding direction.

3. The MRI apparatus of claim 1, wherein the memory stores the at least one program comprising the instructions that, when executed by the processor, further cause the processor to:
   acquire subsampled magnitude image data and subsampled phase image data;
   divide the subsampled magnitude image data and the subsampled phase image data into the plurality of groups, each corresponding to the at least one row of pixels corresponding to the phase encoding direction.

4. The MRI apparatus of claim 1, wherein the memory stores the at least one program comprising the instructions that, when executed by the processor, further cause the processor to dynamically determine the plurality of groups into which the data of the subsampled MR image is divided, using the at least one neural network.

5. The MRI apparatus of claim 1, wherein the memory stores the at least one program comprising the instructions that, when executed by the processor, further cause the processor to:
   acquire data of at least one additional image by circularly shifting the data of the subsampled MR image in a direction corresponding to the phase encoding direction; and
   respectively divide the data of the at least one additional image into the plurality of groups, each corresponding to the at least one row of pixels corresponding to the phase encoding direction.

6. The MRI apparatus of claim 1, wherein the subsampled MR image comprises a subsampled three-dimensional (3D) MR image including a first phase encoding direction and a second phase encoding direction, and
   wherein the memory stores the at least one program comprising the instructions that, when executed by the processor, further cause the processor to:
   divide the data of the subsampled 3D MR image into a plurality of first groups, each corresponding to at least one row of pixels corresponding to the first phase encoding direction; and
   acquire, based on the learning model using the at least one neural network, first reconstructed data respectively corresponding to the plurality of first groups.

7. The MRI apparatus of claim 6, wherein the memory stores the at least one program comprising the instructions that, when executed by the processor, further cause the processor to:
   divide the first reconstructed data respectively corresponding to the plurality of first groups into a plurality of second groups, each corresponding to at least one row of pixels corresponding to the second phase encoding direction;

acquire second reconstructed data respectively corresponding to the plurality of second groups based on the learning model using the at least one neural network; and obtain the reconstructed image corresponding to the subsampled 3D MR image by using the acquired second reconstructed data.

8. The MRI apparatus of claim 1, further comprising a multi-channel radio frequency (RF) coil configured to receive MR signals from an object,
wherein the memory stores the at least one program comprising the instructions that, when executed by the processor, further cause the processor to:
acquire the data of the subsampled MR image corresponding to the multi-channel RF coil; and
obtain the reconstructed image, based on a sensitivity of the multi-channel RF coil and the reconstructed data.

9. The MRI apparatus of claim 1, further comprising a multi-channel radio frequency (RF) coil configured to receive MR signals from an object,
wherein the memory stores the at least one program comprising the instructions that, when executed by the processor, further cause the processor to acquire, based on the MR signals received via the multi-channel RF coil, the data of the subsampled MR image obtained by subsampling in a regular or irregular pattern along the phase encoding direction.

10. An image reconstruction method comprising:
acquiring data of at least one subsampled magnetic resonance (MR) image and data of at least one fully sampled MR image;
obtaining a learning model using at least one neural network by learning correlations between the at least one subsampled MR image and the at least one fully sampled MR image in units of at least one row of pixels corresponding to a phase encoding direction;
acquiring data of a subsampled MR image;
dividing the data of the subsampled MR image into a plurality of groups, each corresponding to the at least one row of pixels corresponding to the phase encoding direction;
acquiring, based on the learning model using the at least one neural network, reconstructed data respectively corresponding to the plurality of groups with respect to the at least one row of pixels corresponding to the phase encoding direction of the data of the subsampled MR image; and
obtaining a reconstructed image corresponding to the subsampled MR image, by using the acquired reconstructed data.

11. The image reconstruction method of claim 10, wherein the acquiring of the data of the subsampled MR image comprises respectively acquiring subsampled real image data and subsampled imaginary image data, and
wherein the dividing of the data of the subsampled MR image into the plurality of groups comprises respectively dividing the subsampled real image data and the subsampled imaginary image data into the plurality of groups, each corresponding to the at least one row of pixels corresponding to the phase encoding direction.

12. The image reconstruction method of claim 10, wherein the acquiring of the data of the subsampled MR image comprises respectively acquiring subsampled magnitude image data and subsampled phase image data, and
wherein the dividing of the data of the subsampled MR image into the plurality of groups comprises respectively dividing the subsampled magnitude image data and the subsampled phase image data into the plurality of groups, each corresponding to the at least one row of pixels corresponding to the phase encoding direction.

13. The image reconstruction method of claim 10, wherein the acquiring of the data of the subsampled MR image comprises acquiring data of at least one additional image by circularly shifting the data of the subsampled MR image in a direction corresponding to the phase encoding direction, and
wherein the dividing of the data of the subsampled MR image into the plurality of groups comprises respectively dividing the data of the subsampled MR image and the data of the at least one additional image into the plurality of groups, each corresponding to the at least one row of pixels corresponding to the phase encoding direction.

14. The image reconstruction method of claim 10, wherein the subsampled MR image comprises a subsampled three-dimensional (3D) MR image including a first phase encoding direction and a second phase encoding direction,
wherein the dividing of the data of the subsampled MR image into the plurality of groups comprises dividing the data of the subsampled 3D MR image into a plurality of first groups, each corresponding to at least one row of pixels corresponding to the first phase encoding direction, and
wherein the acquiring of the reconstructed data comprises acquiring first reconstructed data respectively corresponding to the plurality of first groups based on the learning model using the at least one neural network.

15. The image reconstruction method of claim 14, further comprising:
dividing the first reconstructed data respectively corresponding to the plurality of first groups into a plurality of second groups, each corresponding to at least one row of pixels corresponding to the second phase encoding direction, and
acquiring second reconstructed data respectively corresponding to the plurality of second groups based on the learning model using the at least one neural network,
wherein the obtaining of the reconstructed image comprises obtaining the reconstructed image corresponding to the subsampled 3D MR image by using the acquired second reconstructed data.

16. The image reconstruction method of claim 10, wherein the acquiring of the data of the subsampled MR image comprises acquiring the data of subsampled MR images corresponding to a multi-channel radio frequency (RF) coil, and wherein the obtaining of the reconstructed image corresponding to the subsampled MR image comprises obtaining the reconstructed image based on sensitivity of the multi-channel RF coil and the reconstructed data.

17. The image reconstruction method of claim 10, further comprising receiving MR signals from an object via a multi-channel radio frequency (RF) coil,
wherein the acquiring of the data of the subsampled MR image comprises acquiring, based on the MR signals received via the multi-channel RF coil, the data of the subsampled MR image obtained by subsampling in a regular or irregular pattern along the phase encoding direction.

18. A computer program product comprising a computer-readable recording medium having recorded thereon a program for executing the image reconstruction method of claim 10 on a computer.

19. A magnetic resonance imaging (MRI) apparatus comprising:
a processor; and
a memory storing at least one program,
wherein the memory stores, when the at least one program is executed by the processor, instructions that cause the processor to perform:
acquiring data of at least one subsampled magnetic resonance (MR) image and data of at least one fully sampled MR image;
obtaining a learning model using at least one neural network by learning correlations between the at least one subsampled MR image and the at least one fully sampled MR image in units of at least one row of pixels corresponding to an aliasing direction in which aliasing occurs in the data of the subsampled MR images;
acquiring data of a subsampled MR image;
dividing the data of the subsampled MR image into a plurality of groups, each corresponding to the at least one row of pixels corresponding to the aliasing direction;
acquiring, based on the learning model using the at least one neural network, reconstructed data respectively corresponding to the plurality of groups; and
obtaining a reconstructed image corresponding to the subsampled MR image, by using the acquired reconstructed data.

20. An image reconstruction method comprising:
acquiring data of at least one subsampled magnetic resonance (MR) image and data of at least one fully sampled MR image;
obtaining a learning model using at least one neural network by learning correlations between the at least one subsampled MR image and the at least one fully sampled MR image in units of at least one row of pixels corresponding to an aliasing direction in which aliasing occurs in the data of the subsampled MR image;
acquiring data of a subsampled MR image;
dividing the data of the subsampled MR image into a plurality of groups, each corresponding to the at least one row of pixels corresponding to the aliasing direction;
acquiring, based on the learning model using the at least one neural network, reconstructed data respectively corresponding to the plurality of groups; and
obtaining a reconstructed image corresponding to the subsampled MR image, by using the acquired reconstructed data.

* * * * *